United States Patent
Bowe et al.

(10) Patent No.: US 10,555,907 B2
(45) Date of Patent: Feb. 11, 2020

(54) CONTROLLED-RELEASE SOLID DOSAGE FORMS OF MESALAMINE

(71) Applicant: Santarus, Inc., Bridgewater, NJ (US)

(72) Inventors: Craig Michael Bowe, Encinatas, CA (US); John Christopher Carter, Keswick (CA); Dana Elaine Moseson, West Lafayette, IN (US); Stephen Paul Levine, Norristown, PA (US)

(73) Assignee: Santarus, Inc., Bridgewater, NJ (US)

( * ) Notice: Subject to any disclaimer, the term of this patent is extended or adjusted under 35 U.S.C. 154(b) by 0 days.

(21) Appl. No.: 16/119,362

(22) Filed: Aug. 31, 2018

(65) Prior Publication Data

US 2019/0231699 A1    Aug. 1, 2019

Related U.S. Application Data

(63) Continuation of application No. 14/383,462, filed as application No. PCT/US2013/292921 on Mar. 6, 2013, now Pat. No. 10,071,058.

(60) Provisional application No. 61/607,726, filed on Mar. 7, 2012.

(51) Int. Cl.
| | |
|---|---|
| *A61K 9/20* | (2006.01) |
| *A61K 31/58* | (2006.01) |
| *A61K 9/28* | (2006.01) |
| *A61K 9/48* | (2006.01) |
| *A61K 31/606* | (2006.01) |

(52) U.S. Cl.
CPC .......... *A61K 9/2077* (2013.01); *A61K 9/2018* (2013.01); *A61K 9/2866* (2013.01); *A61K 9/2886* (2013.01); *A61K 9/4808* (2013.01); *A61K 31/58* (2013.01); *A61K 31/606* (2013.01); *A61K 9/2846* (2013.01)

(58) Field of Classification Search
None
See application file for complete search history.

(56) References Cited

U.S. PATENT DOCUMENTS

| | | | |
|---|---|---|---|
| 6,773,720 B1 * | 8/2004 | Villa | A61K 9/2846 424/450 |
| 2009/0017110 A1 * | 1/2009 | Cherukuri | A61K 9/1647 424/451 |

* cited by examiner

*Primary Examiner* — Nannette Holloman
(74) *Attorney, Agent, or Firm* — Bass, Berry & Sims PLC

(57) ABSTRACT

Described are controlled-release solid dosage forms of mesalamine. In one aspect of the invention the controlled-released solid dosage forms of mesalamine are capsules comprising a plurality of coated mini-tablets. Another aspect of the invention related to a methods of treating a patient suffering from inflammatory bowel disease, comprising the step of administering to the patient a therapeutically effective amount of the solid dosage form. The invention also relates to methods of inducing remission of inflammatory bowel disease and maintaining remission of inflammatory bowel disease. In certain aspects, the inflammatory bowel disease is ulcerative colitis or Crohn's disease.

20 Claims, 10 Drawing Sheets

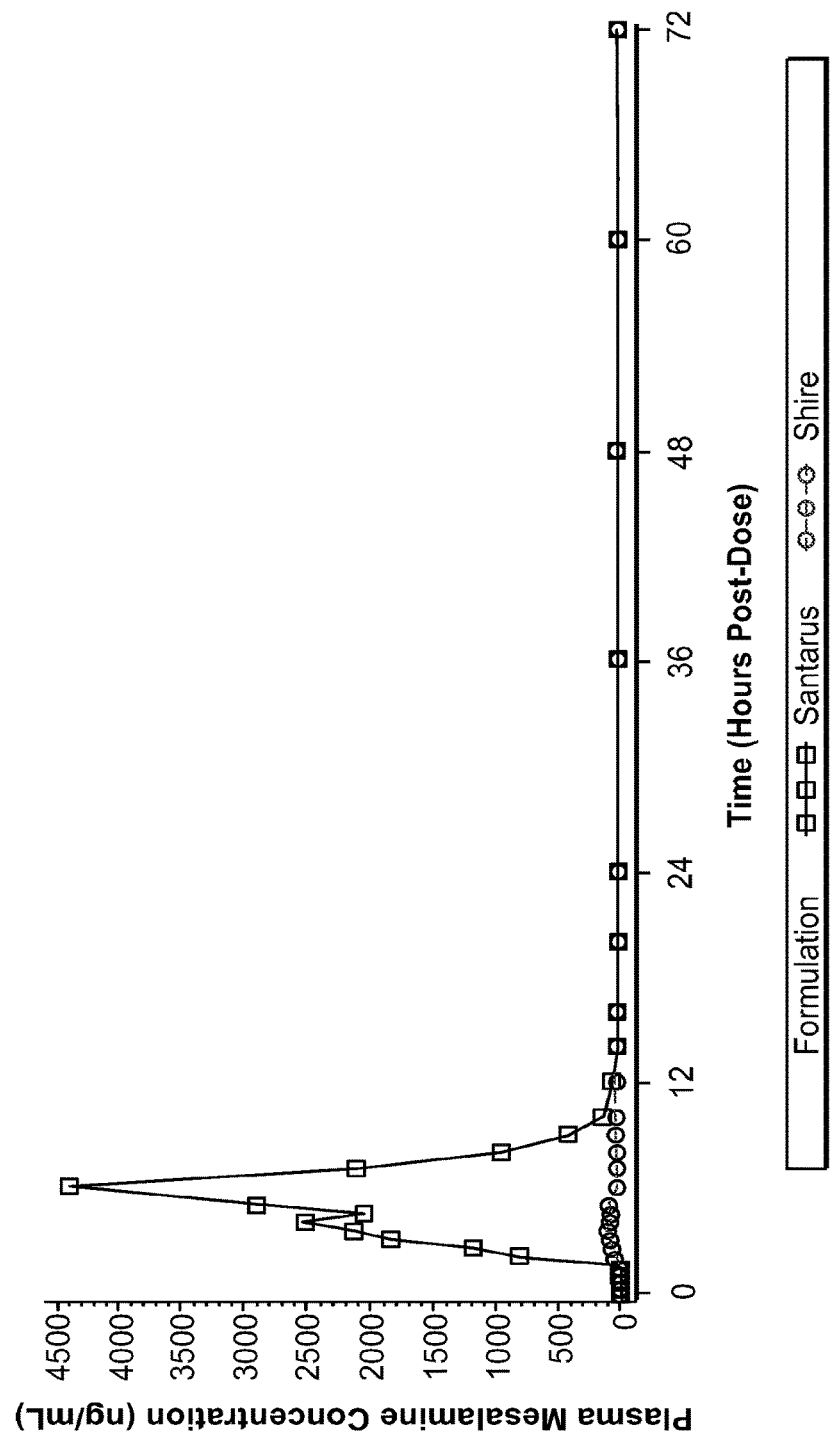

CONTROLLED-RELEASE SOLID DOSAGE FORMS OF MESALAMINE

RELATED APPLICATIONS

This application claims the benefit of priority to U.S. Provisional Patent Application Ser. No. 61/607,726, filed Mar. 7, 2012, the contents of which are hereby incorporated by reference.

BACKGROUND

Inflammatory bowel diseases (IBD), such as ulcerative colitis (UC) and Crohn's disease, are characterized by abdominal pain, bloody diarrhea, and bowel-wall inflammation. Approximately 1 million Americans suffer from UC or Crohn's disease. In Western Europe and the United States the prevalence of UC is 70 to 150 per 100,000, while the prevalence of Crohn's disease is 4 to 100 per 100,000.

Although the cause of IBD is unknown, recent experimental and clinical studies suggest that initiation and pathogenesis of Crohn's disease and UC are multifactorial, involving interactions among genetic, environmental, and immune factors. Recently, IBD has been attributed to abnormal responses to environmental triggers in genetically susceptible individuals. Available data suggest that chronic gut inflammation may result from a dysfunctional immune response to components of normal gut flora. Although no specific bacteria have been implicated in the development of IBD in humans, in genetic models of IBD in mice and rats, specific bacteria have been shown to precipitate disease. In addition, environmental factors other than microbes play a role in the pathogenesis of IBD, as exemplified by the observation that smoking improves UC but worsens Crohn's disease.

There are no curative medical therapies for IBD, and even surgical bowel resection in Crohn's disease is not a definitive cure, since the majority of patients have recurrent disease. Current treatments for IBD fall into six classes: 1) corticosteroids, 2) aminosalicylates, 3) immunosuppressants, 4) antibiotics, 5) biologics, and 6) probiotics.

Aminosalicylate drugs, such as mesalamine (5-amino salicylic acid, or 5-ASA), are the mainstay of treatment for mild and moderate disease. These compounds are typically administered in the form of azo prodrugs, which are activated by colonic bacterial enzymes to release mesalamine as an anti-inflammatory agent. There are several commercially available drugs that contain mesalamine and that are used to treat inflammatory bowel conditions. The manufacturing processes of some of these drugs, however, suffer from inconsistencies, can be difficult to reproduce with the necessary degrees of accuracy and precision, or require specialized and expensive manufacturing equipment. Therefore, there exists a need for a solid dosage form of mesalamine with a high level of drug loading, a similar biological release profile to that of Pentasa®, and that can be manufactured with accuracy and precision.

SUMMARY

Provided herein, in certain embodiments, are multiparticulate dosage forms comprising a plurality of mini-tablets. In one aspect, described herein is a multiparticulate dosage form comprising a plurality of coated mini-tablets wherein each coated mini-tablet comprises a mini-tablet core having a diameter of 2 to 5 mm and comprises an active pharmaceutical agent and optional excipients; an optional undercoat surrounding said core which comprises a water soluble polymer, a topcoat surrounding said optional undercoat that modifies the release of the active pharmaceutical agent; wherein about 65% of said coated mini-tablets exhibit substantially the same release profile.

In another aspect, described herein is a process of manufacturing coated mini-tablets comprising mixing or granulating mixture of active pharmaceutical agent and optional excipients; optionally drying the mixture to a residual amount of water of 0-5%; directly compressing said mixture into mini-tablets having a diameter of 2 to 5 mm; optionally coating the mini-tablets with an optional undercoat composition comprising a water-soluble polymer; and further coating the mini-tablets with a top-coat with a topcoat composition comprising a polymer that modifies release of the active pharmaceutical agent.

In yet another aspect, described herein is a multiparticulate dosage form comprising a plurality of coated mini-tablets wherein each coated mini-tablet comprises a mini-tablet core having a diameter of 2.25 mm and comprises mesalamine, microcrystalline cellulose, hydroxypropyl cellulose, and a lubricant; an optional undercoat surrounding said core which comprises a water soluble polymer, a topcoat which comprises ethylcellulose surrounding said optional undercoat that modifies the release of the active agent; a topcoat which comprises ethylcellulose surrounding said optional undercoat that modifies the release of the active agent; a pore-forming agent in the topcoat; and wherein about 65% of said coated mini-tablets exhibit substantially the same release profile.

In yet another aspect, described herein is a multiparticulate dosage form comprising a plurality of coated mini-tablets wherein each coated mini-tablet comprises a mini-tablet core having a diameter of 2.25 mm and comprises mesalamine, lactose monohydrate, hydroxypropyl cellulose, and a lubricant; an optional undercoat surrounding said core which comprises a water soluble polymer; a topcoat which comprises ethylcellulose surrounding said optional undercoat that modifies the release of the active agent; a pore-forming agent in the topcoat; and wherein about 65% of said coated mini-tablets exhibit substantially the same release profile.

In certain embodiments, the invention relates to a controlled-release solid dosage form, comprising a plurality of mini-tablets, wherein each mini-tablet comprises:
  (a) a core, comprising mesalamine; and
  (b) a coating, comprising low-viscosity ethyl cellulose; and a pore-forming agent selected from the group consisting of hydroxypropyl cellulose and hydroxypropyl methylcellulose;
  wherein the coating surrounds the core.

In certain embodiments, the invention relates to any one of the aforementioned solid dosage forms, wherein the core further comprises a diluent.

In certain embodiments, the invention relates to any one of the aforementioned solid dosage forms, wherein the core further comprises a binder.

In certain embodiments, the invention relates to any one of the aforementioned solid dosage forms, wherein the core further comprises a lubricant.

In certain embodiments, the invention relates to any one of the aforementioned solid dosage forms, wherein the coating further comprises a plasticizer.

In certain embodiments, the invention relates to any one of the aforementioned solid dosage forms, wherein the solid dosage form is a capsule.

In certain embodiments, the invention relates to any one of the aforementioned solid dosage forms, wherein the solid dosage form is a capsule; and the capsule comprises the plurality of mini-tablets.

In certain embodiments, the invention relates to a controlled-release solid dosage form, comprising:
(a) mesalamine in an amount effective for treating inflammatory bowel disease; and
(b) means for topically delivering in the gastrointestinal tract the effective amount of mesalamine.

In certain embodiments, the invention relates to a controlled-release solid dosage form, comprising:
(a) mesalamine in an amount effective for inducing remission of inflammatory bowel disease; and
(b) means for topically delivering in the gastrointestinal tract the effective amount of mesalamine.

In certain embodiments, the invention relates to a controlled-release solid dosage form, comprising:
(a) mesalamine in an amount effective for maintaining remission of inflammatory bowel disease; and
(b) means for topically delivering in the gastrointestinal tract the effective amount of mesalamine.

In certain embodiments, the invention relates to a controlled-release solid dosage form, comprising a plurality of mini-tablets, wherein each mini-tablet comprises:
(a) a core, comprising mesalamine in about 80% by weight of the core; lactose in about 16% by weight of the core; hydroxypropyl cellulose in about 3% by weight of the core; and a lubricant in about 1% by weight of the core; and
(b) a coating, comprising low-viscosity ethyl cellulose; a pore-forming agent; and triethyl citrate;
wherein the coating surrounds the core; and the coating comprises from about 1% to about 6% by weight of the mini-tablet.

In certain embodiments, the invention relates to a method of treating inflammatory bowel disease, comprising the step of orally administering to a mammal in need thereof a therapeutically effective amount of any one of the aforementioned solid dosage forms.

In certain embodiments, the invention relates to a method of inducing remission of inflammatory bowel disease, comprising the step of orally administering to a mammal in need thereof a therapeutically effective amount of any one of the aforementioned solid dosage forms.

In certain embodiments, the invention relates to a method of maintaining remission of inflammatory bowel disease, comprising the step of orally administering to a mammal in need thereof a therapeutically effective amount of any one of the aforementioned solid dosage forms.

In certain embodiments, the invention relates to any one of the aforementioned methods, wherein the inflammatory bowel disease is ulcerative colitis.

In certain embodiments, the invention relates to any one of the aforementioned methods, wherein the inflammatory bowel disease is Crohn's disease.

BRIEF DESCRIPTION OF THE FIGURES

FIG. 5A is a linear plot, without error bars; FIG. 5B is a linear plot with error bars; FIG. 5C is a semi-log plot without error bars; and FIG. 5D is a semi-log plot with error bars.

FIG. 7 depicts a linear plot of mean plasma mesalamine concentrations versus time following administration of Treatments A and B.

DETAILED DESCRIPTION

For convenience, before further description of the invention, definitions of certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to." "Including" and "including but not limited to" are used interchangeably.

The term "patient" refers to a mammal in need of a particular treatment. In certain embodiments, a patient is a primate, canine, feline, or equine. In certain embodiments, a patient is a human.

The terms "co-administration" and "co-administrating" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

FIG. 5 depicts the mean plasma mesalamine concentrations versus time following administration of Treatments A and B. (a) linear plot, without error bars; (b) linear plot with error bars; (c) semi-log plot without error bars; and (d) semi-log plot with error bars.

Figure 6:
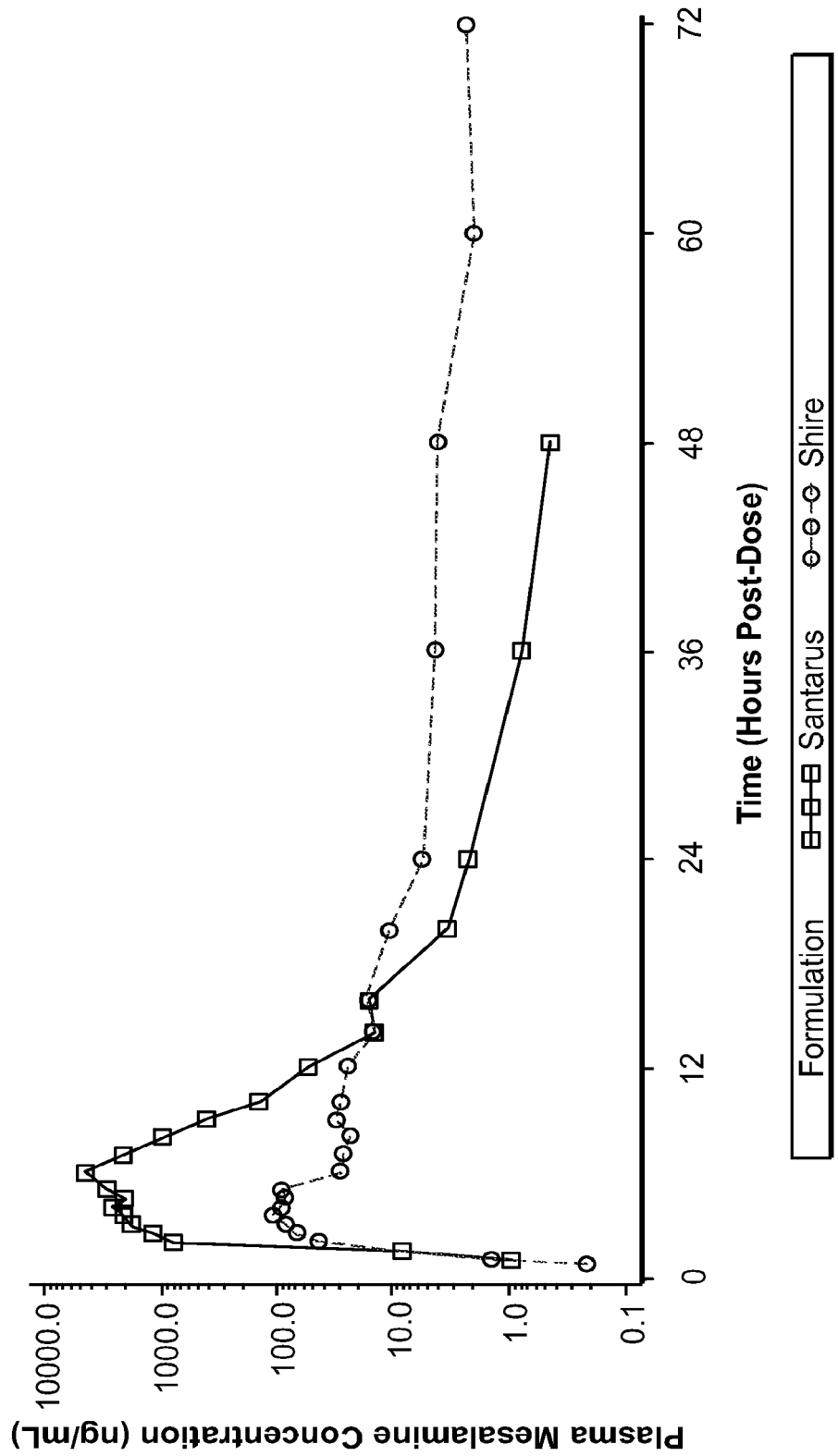
FIG. 6 depicts a semi-log plot of mean plasma mesalamine concentrations versus time following administration of Treatments A and B.

FIG. 6 depicts a semi-log plot of mean plasma mesalamine concentrations versus time following administration of Treatments A and B.

FIG. 7 depicts a linear plot of mean plasma mesalamine concentrations versus time following administration of Treatments A and B.

DETAILED DESCRIPTION

For convenience, before further description of the invention, definitions of certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to." "Including" and "including but not limited to" are used interchangeably.

The term "patient" refers to a mammal in need of a particular treatment. In certain embodiments, a patient is a primate, canine, feline, or equine. In certain embodiments, a patient is a human.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "solvate" refers to a pharmaceutically acceptable form of a specified compound, with one or more solvent molecules, that retains the biological effectiveness of such compound. Examples of solvates include compounds of the invention in combination with solvents such as, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

In certain embodiments, the invention provides pharmaceutically acceptable compositions comprising a therapeutically-effective amount of mesalamine, formulated together with one or more pharmaceutically acceptable carriers (additives) and/or diluents. As described in detail below, the pharmaceutical compositions of the invention may be specially formulated for administration in solid form, including those adapted for oral administration (for example, tablets and encapsulated tablets).

The phrase "therapeutically-effective amount" as used herein means that amount of a therapeutic agent in a composition of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. Proper fluidity can be maintained, for example, by the product of coating materials, such as lecithin, by the maintenance of the required particle size in the case of dispersions, and by the product of surfactants.

Specific examples of pharmaceutically acceptable carriers and excipients that may be used to formulate oral dosage forms am described in the Handbook of Pharmaceutical Excipients, American Pharmaceutical Association (1986).

The term "LSM" as used herein means "least squares-means."

The term "Treatment A" as used herein means a controlled-release solid dosage form, with a composition as described in Example 21.

The term "Treatment B" as used herein means Pentasa®, mesalamine controlled release capsules comprising 500 mg mesalamine, manufactured for Shire U.S., Inc., and approved by the United States Food and Drug Administration (FDA) under approved New Drug Application No. 020049.

Mesalamine is capable of forming pharmaceutically-acceptable salts. The term "pharmaceutically-acceptable salts" in this respect, refers to the relatively non-toxic, inorganic and organic acid addition salts of mesalamine. These salts can be prepared in situ in the administration vehicle or the dosage form manufacturing process, or by separately mesalamine with a suitable organic or inorganic compound, and isolating the salt thus formed during subsequent purification.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In certain embodiments, a formulation of the invention comprises an excipient selected from the group consisting of cyclodextrins, celluloses, liposomes, micelle forming agents, e.g., bile acids, and polymeric carriers, e.g., polyesters and polyanhydrides. In certain embodiments, an aforementioned formulation renders orally bioavailable a composition of the invention.

Prevention of the action of microorganisms upon the subject compounds may be ensured by the inclusion or various antibacterial and antifungal agents, for example, paraben, chlorobutanol, phenol sorbic acid, and the like. It may also be desirable to include isotonic agents, such as sugars, sodium chloride, and the like into the compositions.

Methods of preparing these formulations or compositions include the step of bringing into association mesalamine with the carrier and, optionally, one or more accessory ingredients. In general, the formulations are prepared by uniformly and intimately bringing into association mesalamine with liquid carriers, or finely divided solid carriers, or both, and then, if necessary, shaping the product.

In certain embodiments, formulations of the invention include those suitable for oral administration. The formulations may conveniently be presented in unit dosage form and may be prepared by any methods well known in the art of pharmacy. The amount of active ingredients which can be combined with a carrier material to produce a single dosage form will vary depending upon the host being treated and the particular mode of administration. The amount of active ingredients which can be combined with a carrier material to produce a single dosage form will generally be those amounts of the compounds which produce a therapeutic effect. Formulations of the invention suitable for oral administration may be in the form of capsules, tablets, capsules encompassing tablets, or capsules comprising a plurality of mini-tablets. In one embodiment is provided a dosage form comprising a capsule, the capsule comprising a plurality of mini-tablets, each mini-tablet comprising a core comprising a pharmaceutically active ingredient, such as mesalamine, and one or more pharmaceutically acceptable excipients, the core being coated with a coating material comprising a hydrophobic and a hydrophilic polymer.

Multiparticulate pharmaceutical dosage formulations as described herein contain coated mini-tablets that comprise mini-tablet cores with an active pharmaceutical agent and any optional excipients. In one embodiment, the mini-tablet cores are made by first mixing or granulating an active pharmaceutical agent along with any optional excipients to obtain a compressible blend. In some embodiments, the mini-tablet cores are microcrystalline cellulose based. In some embodiments, the mini-tablet cores are lactose based. Mixing or granulation can be achieved by any known method and can include high shear mixing (impeller and chopper), wet granulation or dry granulation. The employed mixing or granulation method is dependent on the identity of the active pharmaceutical agent as well as any added excipients. Suitable equipment for mixing or granulation comprise Bohle Vagumators, Gral Granulators, Key International KG-5 Granulators, or the like.

In some embodiments, mini-tablet cores contain between about 0.01 mg to about 20 mg of active pharmaceutical agent per core. In certain instances, mini-tablet cores contain between about 1 mg to about 15 mg of active pharmaceutical agent per core and in other instances, mini-tablet cores contain between about 5 mg to about 10 mg, about 5 mg to about 9 mg, about 5 mg to about 8 mg, about 5 mg, about 6 mg, about 7 mg, about 9 mg, about 10 mg, about 11 mg, about 12 mg, about 13 mg, about 14 mg, about 15 mg, about 16 mg, about 17 mg, about 18 mg, about 19 mg, or about 20 mg of active pharmaceutical agent per core. In some embodiments, mini-tablet cores contain about 7.8 mg of active pharmaceutical agent per core. Mini-tablet cores and their coated forms can collectively be aggregated together to provide dosage forms of about 1 mg to about 2000 mg of active pharmaceutical agent; about 100 mg to about 800 mg of active pharmaceutical agent; about 200 mg, about 250 mg, about 400 mg, about 500 mg, about 600 mg, or about 800 mg active pharmaceutical agent.

For wet granulations, the wet granules are subjected to a drying process facilitated by a fluid bed dryer, microwave, nitrogen drying, evaporation, vacuum drying or heatable jacketed process vessel wall. The drying process can be combined with heat of about 50° C., about 60° C., about 70° C., about 80° C., about 90° C., about 100° C., or a temperature effective to dry the wet granulations without degrading the active pharmaceutical agent and/or excipients. The resultant dried granules have a residual amount of water of about 0.5% to about 10%, or about 1% to about 10%. The control of the residual water content in the dried granules may be made for example, by taking samples of the dried granules and annealing them in an oven with an oven temperature of about 80° C. to about 125° C., for example about 90° C., about 95° C., about 100° C., or about 105° C., while measuring water loss.

In wet and dry granulations, the dried granules are passed through mesh screens of size, for example #20 US, #25 US, #30 US, #35 US or #40 US, #45 US, or #75 US, and collected to be compressed into mini-tablets. Granules that do not pass through the desired mesh size are optionally subjected to an oscillator (Erweka AMD) or additional milling or other processing followed by passage through additional one or more mesh screens.

The granules or mixed powders are compressed into mini-tablet cores with diameters of about 1.5 mm to about 7 mm, such as, for example, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, about 5.25 mm, about 5.5 mm, about 5.75 mm, about 6 mm, about 6.25 mm, about 6.5 mm, about 6.75 mm, or about 7 mm in diameter. In one embodiment, granules or mixed powders are compressed into mini-tablet cores with diameters of 2.25 mm, or about 2.5 mm. Lubricants are added to the tableting procedure to prevent tablets from sticking to the tablet dies and punches. Lubricant concentrations range from under 1% to about 5% of the total tablet mass, for example about 0.5%, about 1%, about 2%, about 3%, about 4% or about 5%. Mini-tablet cores can be compressed into any shape including but not limited to spherical, flat disk, capsule, convex, concave, polygonal or the like. Suitable tableting equipment include rotary tablet machines such as Vector-Colton 2216, Stokes/Pennwalt 555-2 or Manesty Betapress.

In solid dosage forms of the invention for oral administration (capsules, capsules comprising a plurality of mini-tablets, tablets, and the like), the active ingredients are mixed with one or more pharmaceutically-acceptable carriers, such as sodium citrate or dicalcium phosphate, and/or any of the following: (1) fillers or extenders, such as starches, microcrystalline cellulose, lactose, sucrose, glucose, mannitol, and/or silicic acid; (2) binders, such as, for example, hydroxypropyl cellulose, hydroxypropyl methylcellulose, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like. In certain embodiments, the manufacture of tablets, capsules, or capsules comprising a plurality of mini-tablets is more reliable and cost-effective than methods of manufacturing other particulate-based solid dosage forms.

A tablet may be made by compression or molding, optionally with one or more accessory ingredients. Compressed tablets may be prepared using binder (for example, gelatin or hydroxypropyl cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, mini-tablets, and other solid dosage forms of the pharmaceutical compositions of the invention, such as dragees, capsules, pills and granules, may optionally be scored or prepared with coatings and shells, such as enteric coatings and other coatings. They may also be formulated so as to provide slow or controlled release of the active ingredients therein using, for example, ethyl cellulose, hydroxypropyl cellulose, hydroxypropylmethyl cellulose, and combinations thereof, in varying proportions to provide the desired release profile, other polymer matrices. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredients only in a certain portion of the gastrointestinal tract, optionally, in a delayed manner. Examples of embedding compositions which can be used include polymeric substances.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes.

Actual dosage levels of mesalamine in the pharmaceutical compositions of this invention may be varied so as to obtain an amount of an active ingredient which is effective to achieve the desired therapeutic response for a particular patient, composition, and mode of administration, without being toxic to the patient.

The selected dosage level will depend upon a variety of factors including the activity of mesalamine, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of mesalamine employed in the pharmaceutical composition at levels lower than that required in order to achieve the desired therapeutic effect and gradually increase the dosage until the desired effect is achieved.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

In certain embodiments, hydrophilic polymers suitable for use in the invention as pore-forming agents are readily water-soluble and are tolerated in vivo without toxic effects (i.e., are biocompatible). Suitable polymers include hydroxypropyl cellulose, hydroxypropyl methylcellulose, polyethylene glycol (PEG), polylactic (also termed polylactide), polyglycolic acid (also termed polyglycolide), a polylactic-polyglycolic acid copolymer, and polyvinyl alcohol. In certain embodiments, the polymers are those having a molecular weight of about 100 or 120 daltons up to about 5,000 or 10,000 daltons, or from about 300 daltons to about 5,000 daltons. In certain embodiments, the polymer is polyethyleneglycol having a molecular weight of about 100 to about 5,000 daltons, or having a molecular weight of about 300 to about 5,000 daltons. In certain embodiments, the polymer is polyethyleneglycol of 750 daltons (PEG(750)). Polymers may also be defined by the number of monomers therein; in certain embodiments of the invention utilizes polymers of at least about three monomers, such PEG polymers consisting of three monomers (approximately 150 daltons).

In certain embodiments, other hydrophilic polymers which may be suitable for use in the invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the invention comprises a biocompatible polymer selected from polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butyric acid), poly(valeric acid), poly(lactide-co-caprolactone), polysaccharides, proteins, polyhyaluronic acids, polycyanoacrylates, and blends, mixtures, or copolymers thereof.

In certain embodiments, the release characteristics of a formulation of the invention depend on the encapsulating material, the concentration of encapsulated drugs, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or encapsulation in different materials can be used to obtain an initial release in the stomach, followed by later release in the intestine. Release can also be manipulated by inclusion of salts or pore forming agents, which can increase water uptake or release of drug by diffusion from the capsule. Excipients that modify the solubility of the drug can also be used to control the release rate. Agents which enhance degradation or release of mesalamine can also be incorporated. They can be added to the drug, added as a separate phase (i.e., as particulates). In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore-forming agents which add microstructure to the matrices (i.e., water soluble compounds, such as inorganic salts and sugars) are added as particulates.

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups, such as cyanoacrylates and methacrylates).

The solid dosage form may be a sustained-release dosage form or a controlled-release dosage form. These formulations, at comparable daily dosages of conventional immediate release drug, are often associated with a lower incidence or severity of adverse drug reactions; and they can also be administered at a lower daily dose than conventional oral medication while maintaining therapeutic activity.

In certain embodiments, "controlled-release" formulations are designed to release initially an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds The term "sustained release" is defined for purposes of the invention as the release of the therapeutic agent from the formulation at such a rate that blood (e.g., plasma) concentrations (levels) are maintained within the therapeutic range (above the minimum effective analgesic concentration or "MEAC") but below toxic levels over a period of lime of about 12 hours or longer.

The therapeutic agents can be formulated as a controlled- or sustained-release oral formulation in any suitable tablet, coated tablet, capsules comprising a plurality of mini-tablets, or encapsulated tablets known to those of ordinary skill in the art.

The tablets may be film coated with a material that permits release of the active agents at a sustained or controlled rate in an aqueous medium. The film coat is chosen so as to achieve, in combination with the other stated properties, a desired in vitro release rate. The sustained-release or controlled-release coating formulations of the invention should be capable of producing a strong, continuous film that is smooth and elegant, capable of supporting pigments and other coating additives, non-toxic, inert, and tack-free.

Suitable optional excipients for use in mini-tablet cores include any commonly used excipients in pharmaceutics and are selected on the basis of compatibility with the active pharmaceutical agent and the release profile properties of the desired dosage form. Excipients include, but are not limited to, binders, fillers, flow aids, disintegrants, lubricants, gelling agents, plasticizers, stabilizers, surfactants, and the like. A summary of excipients described herein, may be found, for example in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer, crospovidone; povidone; starch; pregelatinized starch; tragacanth; dextrin; a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Fillers or diluents increase bulk to facilitate compression of the mini-tablet cores. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinized starch; compressible sugar, such as Di-Pac® (Amstar); hydroxypropylmethylcellulose; sucrose-based diluents; confectioner's sugar, monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; bentonite; and the like.

Flow-aids or glidants improve the flow characteristics of a powder mixtures. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

Disintegrants facilitate breakup or disintegration of the coated mini-tablets after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp; sodium lauryl sulfate; sodium lauryl sulfate in combination starch; and the like.

Lubricants are compounds which prevent, reduce or inhibit adhesion or friction of materials. Exemplary lubricants include, e.g., stearic acid; calcium hydroxide, talc; a hydrocarbon such as mineral oil, or hydrogenated vegetable oil such as hydrogenated soybean oil (Sterotex®), Lubritab®, Cutina®; higher fatty acids and their alkali-metal and alkaline earth metal salts, such as aluminum, calcium, magnesium, zinc, stearic acid, sodium stearates, magnesium stearate, glycerol, talc, waxes, Stearowet®, boric acid, sodium acetate, leucine, a polyethylene glycol or a methoxypolyethylene glycol such as Carbowax™, sodium oleate, glyceryl behenate (Compitrol 888®), glyceryl palmitostearate (Precirol®), colloidal silica such as Syloid™, Carb-O-Sil®, a starch such as corn starch, silicone oil, a surfactant, and the like. Hydrophilic lubricants include, e.g., sodium stearyl fumerate (currently marketed under the trade name PRUV®), polyethylene glycol (PEG), magnesium lauryl sulfate, sodium lauryl sulfate (SLS), sodium benzoate, sodium chloride, and the like.

Gelling agents include compounds such as polyvinylpyrrolidone, e.g., polyvinylpyrmrolidone K12, polyvinylpyrrolidone K17, polyvinylpyrrolidone K25, or polyvinylpyrrolidone K30; polyethylene glycol, e.g., the polyethylene glycol can have a molecular weight of about 300 to about 6000, or about 3350 to about 4000, or about 7000 to about 5400; polysorbate-80; sodium alginate; gums, such as, e.g., gum tragacanth, locust bean gum, gum acacia, carrageenan gum, guar gum; xanthans, including xanthan gum; sugars; cellulosics, such as, e.g., sodium carboxymethylcellulose, ethylcellulose, methylcellulose, sodium carboxymethylcellulose, hydroxypropylmethylcellulose, hydroxypropylcellulose, hydroxyethylcellulose; polysorbate-80; sodium alginate; polyethoxylated sorbitan monolaurate; polyethoxylated sorbitan monolaurate; povidone and the like.

Stabilizers include compounds such as any anti-oxidation agents, e.g., butylated hydroxytoluene (BHT), sodium ascorbate, and tocopherol; buffers, acids, and the like.

Surfactants include compounds such as sodium lauryl sulfate, sorbitan monooleate, polyoxyethylene sorbitan monooleate, polysorbates, polaxomers, bile salts, glyceryl monostearate, copolymers of thylene oxide and propylene oxide, e.g., Pluronic® (BASF); and the like.

The aforementioned excipients are given as examples only and are not meant to include all possible choices. Other suitable excipient classes include coloring agents, granulating agents, preservatives, anti-foaming agents, plasticizers and the like. Additionally, many excipients can have more than one role or function, or can be classified in more than one group; the classifications are descriptive only, and are not intended to limit any use of a particular excipient.

Coating layers, as used herein, refers to completely encasing or coating a mini-tablet core with a pharmaceutically acceptable coating. In addition, coating layers also refer to completely encasing or coating a unit dosage form such as a tablet or capsule that contain or encapsulate coated mini-tablets. Undercoats, topcoats, inner- and outer-coats are various types of coating layers.

The process of applying coating layers can be achieved by any known method such as by using fluidized bed equipment, perforated pans, a regular pharmaceutical pan, compression coating, continuous or short spray methods, high-shear mixing or by drenching. For example, a plasticized dispersion of coating polymer may be applied onto a mini-tablet core comprising an active pharmaceutical agent by spraying using any suitable spray equipment known in the art. Results of a coating procedure may be routinely checked by withdrawing a sample of the coated mini-tablets and determining a release rate of the samples. If the desired amount of release is not achieved, the coating procedure may be repeated until the desired result is obtained. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6.sup.th Ed. (Media, Pa.: Williams & Wilkins, 1995).

Coating layers can optionally contain a plasticizer to prevent the formation of pores and cracks that would permit the penetration of the gastric fluids. Suitable plasticizers include, but are not limited to, triethyl citrate, triacetin (glyceryl triacetate), acetyl triethyl citrate, polyethylene glycols such as PEG 300, PEG 400, PEG 600, PEG 1450, PEG 3350, and PEG 800, Carbowax 400 (polyethylene glycol 400), diethyl phthalate, tributyl citrate, stearic acid, oleic acid, acetylated monoglycerides, glycerol, fatty acid esters, propylene glycol, and dibutyl phthalate. Coating layers can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance of the coated mini-tablet.

In certain embodiments, the dosage forms of the invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release any of the active agent(s) in the desired areas of the gastrointestinal (GI) tract, e.g., the stomach or small intestine, such that an absorption profile is provided which is capable of providing therapeutic benefit to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

In certain embodiments, the substrate (e.g., mini-tablet core) containing one or more therapeutic agent(s) is coated with a hydrophobic material selected from the group consisting of (i) an alkylcellulose; (ii) an acrylic polymer; and (iii) mixtures thereof. The coating may be applied in the form of an organic or aqueous solution or dispersion. The coating may be applied to obtain a weight gain from about 1 to about 25% of the substrate in order to obtain a desired sustained release profile or controlled-release profile. Such formulations are described, e.g., in detail in U.S. Pat. Nos. 5,273,760 and 5,286,493; both incorporated by reference. Other examples of controlled- and sustained-release formulations and coatings which may be used in accordance with the invention include U.S. Pat. Nos. 5,324,351; 5,356,467, and 5,472,712; all incorporated by reference.

Cellulosic materials and polymers, including alkylcelluloses, provide hydrophobic materials well suited for coating the formulations according to the invention. Simply by way of example, one alkylcellulosic polymer is ethylcellulose, although the artisan will appreciate that other cellulose or alkylcellulose polymers may be readily employed, singly or in any combination, as all or part of a hydrophobic coating.

In embodiments of the invention where the coating comprises a hydrophobic material, such as ethyl cellulose, the inclusion of an effective amount of a plasticizer in an aqueous or solvent-based dispersion of hydrophobic material will further improve the physical properties of the coating. Exemplary solvents in which the plasticizer can be dispersed include, but are not limited to, alcohol-based solvents, such as methyl alcohol, ethyl alcohol, n-propyl alcohol, and iso-propyl alcohol. For example, because ethyl cellulose has a relatively high glass transition temperature and does not form flexible films under normal coating conditions, a plasticizer may be incorporated into an ethyl cellulose coating mixture before using the same as a coating material. Generally, the amount of plasticizer included in a coating solution is based on the concentration of the film-former, e.g., most often from about 1 to about 50 percent by weight of the coating mixture. Concentration of the plasticizer, however, can only be properly determined after careful experimentation with the particular coating mixture and method of application.

Examples of suitable plasticizers for ethyl cellulose include water insoluble plasticizers, such as dibutyl sebacate, diethyl phthalate, triethyl citrate, tributyl citrate, and triacetin, although it is possible that other water-insoluble plasticizers (such as acetylated monoglycerides, phthalate esters, castor oil) may be used. Triethyl citrate can be a plasticizer for mixtures of ethyl cellulose and pore-forming agents according to embodiments described herein.

In certain embodiments, a mixture of low-viscosity ethyl cellulose, a pore-forming agent, and a plasticizer is used to coat the mini-tablets of the invention. In certain embodiments, the pore-forming agent is hydroxypropyl cellulose or hydroxypropylmethyl cellulose, or mixtures thereof. In certain embodiments, the pore-forming agent is hydroxypropyl cellulose. In certain embodiments, the pore-forming agent is hydroxypropylmethyl cellulose. In certain embodiments, a plurality of the coated mini-tablets is thereafter placed in a gelatin capsule in an amount sufficient to provide an effective controlled release dose when ingested and contacted by an environmental fluid, e.g., gastric fluid or dissolution media. In certain embodiments, the plasticizer is triethylcitrate.

In certain embodiments, the gelatin capsule comprises from 30 to 100 mini-tablets, from 32 to 70 mini-tablets, from 32 to 68 mini-tablets, from 32 to about 64 mini-tablets, from 50 to 100 mini-tablets, from 60 to 100 mini-tablets, or from 70 to 100 mini-tablets. In certain embodiments, the gelatin capsule comprises 32 mini-tablets, 40 mini-tablets, 45 mini-tablets, 50 mini-tablets, 55 mini-tablets, 60 mini-tablets, 61 mini-tablets, 62 mini-tablets, 63 mini-tablets, 64 mini-tablets, 65 mini-tablets, 66 mini-tablets, 67 mini-tablets, 68 mini-tablets, 69 mini-tablets, 70 mini-tablets, 71 mini-tablets, 72 mini-tablets, 73 mini-tablets, 74 mini-tablets, 75 mini-tablets, 76 mini-tablets, 77 mini-tablets, 78 mini-tablets, 79 mini-tablets, 80 mini-tablets, 81 mini-tablets, 82 mini-tablets, 83 mini-tablets, 84 mini-tablets, 85 mini-tablets, 86 mini-tablets, 87 mini-tablets 88 mini-tablets, 89 mini-tablets, 90 mini-tablets, 91 mini-tablets, 92 mini-tablets, 93 mini-tablets, 94 mini-tablets, 95 mini-tablets, 96 mini-tablets, 97 mini-tablets, 98 mini-tablets, 99 mini-tablets, or 100 mini-tablets.

In some embodiments, each mini-tablet comprises from about 2 mg about 10 mg, about 3 mg to about 10 mg, about 3.5 mg to about 10 mg, about 3.5 mg to about 10 mg, about 3.5 mg to about 10 mg, about 3.5 mg to about 9 mg, or about 3.5 mg to about 8 mg of a pharmaceutically active ingredient, such as mesalamine. In some embodiments, each mini-tablet comprises about 2 mg, about 2.5 mg, about 3 mg, about 3.5 mg, about 3.6 mg, about 3.7 mg, about 3.8 mg, about 3.9 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 7.8 mg, about 8 mg, about 8.25 mg, about 8.5 mg, about 8.75 mg, about 9 mg, about 9.25 mg, about 9.5 mg, about 9.75 mg, or about 10 mg of a pharmaceutically active ingredient, such as mesalamine. In some embodiments, each mini-tablet comprises about 7.8 mg of a pharmaceutically active ingredient, such as mesalamine.

In some embodiments, each coated mini-tablet comprises from about 40% to about 90% weight percent, about 45% to about 90% weight percent, about 50% to about 90% weight percent, about 55% to about 90% weight percent, about 60% to about 90% weight percent, about 65% to about 90% weight percent, about 70% to about 90% weight percent, about 75% to about 90% weight percent, or about 80% to about 90% weight percent mesalamine by weight of the mini-tablet.

In some embodiments, each mini-tablet core comprises from about 40% to about 90% weight percent, about 45% to about 90% weight percent, about 50% to about 90% weight percent, about 55% to about 90% weight percent, about 60% to about 90% weight percent, about 65% to about 90% weight percent, about 70% to about 90% weight percent, about 75% to about 90% weight percent, or about 80% to about 90% weight percent mesalamine by weight of the mini-tablet core.

The controlled release solid dosage form of the invention slowly releases the therapeutically active agent, such as mesalamine, for example, when ingested and exposed to gastric fluids, and then to intestinal fluids. The controlled release profile of the formulations of the invention can be altered, for example, by varying the amount of coating, by altering the manner in which the plasticizer is added to the coating mixture, by varying the amount of plasticizer relative to other coating components, by the inclusion of additional ingredients or excipients, by altering the method of manufacture or other process variables that are known to those of ordinary skill in the art. The dissolution profile of the ultimate product may also be modified, for example, by increasing or decreasing the thickness of the coating.

The controlled release profile of the formulations of the invention can be altered, for example, by varying the amounts of and ratios between one or more hydrophilic polymers, such as hydroxypropyl methyl cellulose or hydroxypropyl cellulose, for example, and one or more hydrophobic polymers, such as ethyl cellulose, for example, that comprise the coating.

In certain embodiments, the coating mixtures of the invention may contain, in addition to the low-viscosity ethyl cellulose, the pore-forming agent, and the plasticizer, a colorant to provide elegance and product distinction.

The coating may be applied onto the substrate comprising the one or more therapeutically active agent (e.g., the tablet core) by spraying using any suitable spray equipment known in the art. In certain embodiments, a Wurster fluidized-bed system is used in which an air jet, injected from underneath, fluidizes the coating material and effects drying while the coating is sprayed on.

In certain embodiments, the release of the therapeutically active agent from the controlled release formulation of the invention can be further influenced, i.e., adjusted to a desired rate, by the addition of one or more release-modifying agents, or by providing another passageway through the coating. The ratio of hydrophobic material to pore-forming material is determined by, among other factors, the release rate required and the solubility characteristics of the materials selected.

The release-modifying agents, which function as pore-forming agents, may be organic or inorganic, and include materials that can be dissolved, extracted or leached from the coating in the environment of use. The pore-formers may comprise one or more hydrophilic materials, such as hydroxypropylmethylcellulose.

The coatings of the invention can also include erosion-promoting agents, such as starch and gums.

In certain embodiments, the coatings of the invention can also include materials useful for making microporous lamina in the environment of use, such as polycarbonates comprised of linear polyesters of carbonic acid in which carbonate groups reoccur in the polymer chain. The release-modifying agent may also comprise a semi-permeable polymer.

In certain embodiments, the release-modifying agent is selected from the group consisting of hydroxypropylmethylcellulose, lactose, metal stearates, and mixtures of any of the foregoing.

In certain embodiments, the coatings of the invention may also include an exit means comprising at least one passageway, orifice, or the like. The passageway may be formed by such methods as those disclosed in U.S. Pat. Nos. 3,845,770; 3,916,889; 4,063,064; and 4,088,864; all incorporated by reference. The passageway can have any shape, such as round, triangular, square, elliptical, or irregular.

In certain embodiments, the sustained-release or controlled-release formulations of the invention may slowly release the therapeutically active agents, e.g., when ingested and exposed to gastric fluids, and then to intestinal fluids. The sustained release or controlled-release profile can be altered, for example, by varying the amount of retardant, i.e., hydrophobic material, by varying the amount of plasticizer relative to hydrophobic material, by the inclusion of additional ingredients or excipients, by altering the method of manufacture.

In one embodiment, the plurality of coated mini-tablets is incorporated into a solid unit dosage form. The term "solid unit dosage form" means a dosage form intended to be swallowed as a single unit that is selected from a hard or soft capsule. In one embodiment, the solid unit dosage forms are selected from soft capsules or hard capsules of any size or shape. Suitable capsules, include but are not limited to, spherical or elliptical soft elastic gelatin capsules; starch, cellulose or gelatin hard capsules such as Capill®, and the like. Appropriate capsule sizes are selected based on the number and size of the coated mini-tablets to be incorporated and include capsule sizes 000, 00EL, 00, 0EL, 0, 1, 2, 3, 4 or 5. In some embodiments, a capsule comprises from 30 to 100 mini-tablets, from 32 to 70 mini-tablets, from 32 to 68 mini-tablets, from 32 to about 64 mini-tablets, from about 50 to about 100 mini-tablets, from about 60 to about 100 mini-tablets, or from about 70 to about 100 mini-tablets. In certain embodiments, the gelatin capsule comprises 32 mini-tablets, 40 mini-tablets, 45 mini-tablets, 50 mini-tablets, 55 mini-tablets, 60 mini-tablets, 61 mini-tablets, 62 mini-tablets, 63 mini-tablets, 64 mini-tablets, 65 mini-tablets, 66 mini-tablets, 67 mini-tablets, 68 mini-tablets, 69 mini-tablets, 70 mini-tablets, 71 mini-tablets, 72 mini-tablets, 73 mini-tablets, 74 mini-tablets, 75 mini-tablets, 76 mini-tablets, 77 mini-tablets, 78 mini-tablets, 79 mini-tablets, 80 mini-tablets, 81 mini-tablets, 82 mini-tablets, 83 mini-tablets, 84 mini-tablets, 85 mini-tablets, 86 mini-tablets, 87 mini-tablets, 88 mini-tablets, 89 mini-tablets, 90 mini-tablets, 91 mini-tablets, 92 mini-tablets, 93 mini-tablets, 94 mini-tablets, 95 mini-tablets, 96 mini-tablets, 97 mini-tablets, 98 mini-tablets, 99 mini-tablets, or 100 mini-tablets.

In some instances, a capsule containing coated mini-tablets is-itself further coated with a delayed release or enteric coating as described herein.

In some instances, the mini-tablets themselves may further comprise an enteric coating, as described herein.

One aspect of the invention relates to combination therapy. This type of therapy is advantageous because the co-administration of active ingredients achieves a therapeutic effect that is greater than the therapeutic effect achieved by administration of only a single therapeutic agent.

In certain embodiments, a subject suffering from inflammatory bowel disease, such as ulcerative colitis or Crohn's disease, is administered a solid dosage form comprising mesalamine according to the present invention in combination with an additional therapeutic agent in order to treat such inflammatory bowel disease or to prevent its recurrence. In some embodiments, the additional therapeutic agent comprises other dosage forms comprising mesalamine or steroids, such as budesonide. Additional therapeutic agents comprising mesalanine and their uses in the treatment of inflammatory bowel disease are described in U.S. Pat. Nos. 6,551,620, 6,773,720, 5,541,170, 5,541,171, and 6,893,662, all of which are hereby incorporated by reference in their entirety. Additional therapeutic agents comprising steroids, such as budesonide, and their uses in the treatment of inflammatory bowel diseases are described in U.S. Pat. Nos. 6,423,340, 5,643,602, 7,431,943, 7,410,651, 8,029,823, all of which are hereby incorporated by reference in their entirety.

In certain embodiments, the co-administration of two or more therapeutic agents achieves a therapeutic effect that is greater than the therapeutic effect achieved by administration of only a single therapeutic agent. In this regard, the combination therapies are efficacious. The therapeutic effect of one therapeutic agent is augmented by the co-administration of another therapeutic agent.

In certain embodiments, the co-administration of two or more therapeutic agents achieves a therapeutic effect that is equal to about the sum of the therapeutic effects achieved by administration of each single therapeutic agent. In these embodiments, the combination therapies are said to be "additive."

In certain embodiments, the co-administration of two or more therapeutic agents achieves a synergistic effect, i.e., a therapeutic effect that is greater than the sum of the therapeutic effects of the individual components of the combination.

The therapeutic agents may be administered as separate compositions. One or more active agent may be administered at the same time as the other active agent(s) or the active agents may be administered intermittently. The length of time between administrations of the therapeutic agents may be adjusted to achieve the desired therapeutic effect. In certain instances, one or more therapeutic agent(s) may be administered only a few minutes (e.g., about 1, 2, 5, 10, 30, or 60 min) after administration of the other therapeutic agent(s). Alternatively, one or more therapeutic agent(s) may be administered several hours (e.g., about 2, 4, 6, 10, 12, 24, or 36 h) after administration of the other therapeutic agent(s). In certain embodiments, it may be advantageous to administer more than one dosage of one or more therapeutic agent(s) between administrations of the remaining therapeutic agent(s). For example, one therapeutic agent may be administered at 2 hours and then again at 10 hours following administration of the other therapeutic agent(s). Importantly, it is required that the therapeutic effects of each active ingredient overlap for at least a portion of the duration of each therapeutic agent so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For a normal adult having a body weight of about 70 kg, a dosage may range from about 0.1 to about 25 mg/kg body weight. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered.

Importantly, the determination of dosage ranges and optimal dosages for a particular mammal is also well within the ability of one of ordinary skill in the art having the benefit of the instant disclosure.

In certain embodiments, it may be advantageous for the pharmaceutical combination to have a relatively large amount of the first component compared to the second component. In certain instances, the ratio of the first active agent to second active agent is about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, or 5:1. In certain embodiments, it may be preferable to have a more equal distribution of pharmaceutical agents. In certain instances, the ratio of the first active agent to the second active agent is about 4:1, 3:1, 2:1, 1:1, 1:2, 1:3, or 1:4. In certain embodiments, it may be advantageous for the pharmaceutical combination to have a relatively large amount of the second component compared to the first component. In certain instances, the ratio of the second active agent to the first active agent is about 30:1, 20:1, 15:1, 10:1, 9:1, 8:1, 7:1, 6:1, or 5:1. In certain instances, the ratio of the second active agent to first active agent is about 100:1, 90:1, 80:1, 70:1, 60:1, 50:1, or 40:1. In certain instances, the ratio of the second active agent to first active agent is about 200:1, 190:1, 180:1, 170:1, 160:1, 150:1, 140:1, 130:1, 120:1, or 110:1.

Dosage amount and interval may be adjusted on an individual or group basis to provide plasma levels of a particular active moiety or moieties sufficient to maintain the modulating effects or minimal effective concentration (MEC) of each of them. The MEC will vary for each compound and individual, but it can be estimated from in vitro data. Dosages necessary to achieve the MEC will depend on individual characteristics and route of administration. However, HPLC assays or bioassays can be used to determine plasma concentrations.

The term "synergistic" refers to a combination which is more therapeutically effective than the additive effects of any two or more single agents. A synergistic effect permits the effective treatment of a disease using lower amounts (doses) than individual therapy. The lower doses result in lower toxicity without reduced efficacy. In addition, a synergistic effect can result in improved efficacy. Finally, synergy may result in an improved avoidance or reduction of disease as compared to any single therapy.

Combination therapy can allow for the product of lower doses of the first therapeutic or the second therapeutic agent (referred to as "apparent one-way synergy" herein), or lower doses of both therapeutic agents (referred to as "two-way synergy" herein) than would normally be required when either drug is used alone.

Combination therapy can allow for the product of lower doses of any one of the therapeutic agents (referred to as "apparent one-way synergy" herein), or lower doses of all therapeutic agents than would normally be required when any drug is used alone.

In certain embodiments, the synergism exhibited between one or more therapeutic agent(s) and the remaining therapeutic agent(s) is such that the dosage of one of the therapeutic agents would be sub-therapeutic if administered without the dosage of the other therapeutic agents.

The terms "augmentation" or "augment" refer to combinations where one of the compounds increases or enhances therapeutic effects of another compound or compounds administered to a patient. In some instances, augmentation can result in improving the efficacy, tolerability, or safety, or any combination thereof, of a particular therapy.

In certain embodiments, the invention relates to a pharmaceutical composition comprising a therapeutically effective dose of one or more therapeutic agent(s) together with a dose of another therapeutic agent effective to augment the therapeutic effect of the one or more therapeutic agent(s). In other embodiments, the invention relates to methods of augmenting the therapeutic effect in a patient of one or more therapeutic agent(s) by administering another therapeutic agent to the patient.

In certain embodiments, the invention is directed in part to synergistic combinations of one or more therapeutic agent(s) in an amount sufficient to render a therapeutic effect together with the remaining therapeutic agent(s). For example, in certain embodiments a therapeutic effect is attained which is at least about 2 (or at least about 4, 6, 8, or 10) times greater than that obtained with the dose of the one or more therapeutic agent(s) alone. In certain embodiments, the synergistic combination provides a therapeutic effect which is up to about 20, 30 or 40 times greater than that obtained with the dose of the one or more therapeutic agent(s) alone. In such embodiments, the synergistic combinations display what is referred to herein as an "apparent one-way synergy", meaning that the dose of the remaining therapeutic agent(s) synergistically potentiates the effect of the one or more therapeutic agent(s), but the dose of the one or more therapeutic agent(s) does not appear to significantly potentiate the effect of the remaining therapeutic agent(s).

In certain embodiments, the combination of active agents exhibits two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy may be evaluated by biological activity assays. For example, the therapeutic agents are mixed at molar ratios designed to give approximately equipotent therapeutic effects based on the $EC_{90}$ values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic or additive or augmented effects provided by the inventive combination of the first and second therapeutic agent, it may be possible to use reduced dosages of each of therapeutic agent. Due to the synergistic or additive or augmented effects provided by the inventive combination of the first, second, and third therapeutic agents, it may be possible to use reduced dosages of each of therapeutic agent. By using lesser amounts of drugs, the side effects associated with each may be reduced in number and degree. Moreover, the inventive combinations avoid side effects to which some patients are particularly sensitive.

In certain embodiments, the invention relates to a controlled-release solid dosage form, comprising a plurality of mini-tablets, wherein each mini-tablet comprises:
(a) a core, comprising mesalamine; and
(b) a coating, comprising low-viscosity ethyl cellulose; and a pore-forming agent selected from the group consisting of hydroxypropyl cellulose and hydroxypropyl methylcellulose;
wherein the coating surrounds the core.

In certain embodiments, the invention relates to any one of the aforementioned solid dosage forms, wherein the core further comprises a diluent.

In certain embodiments, the invention relates to any one of the aforementioned solid dosage forms, wherein the core further comprises a binder.

In certain embodiments, the invention relates to any one of the aforementioned solid dosage forms, wherein the core further comprises a lubricant.

In certain embodiments, the invention relates to any one of the aforementioned solid dosage forms, wherein the coating further comprises a plasticizer.

In certain embodiments, the invention relates to a controlled-release solid dosage form, comprising a plurality of mini-tablets, wherein each mini-tablet comprises:
(a) a core, comprising mesalamine; a diluent; a binder; and a lubricant; and
(b) a coating, comprising low-viscosity ethyl cellulose; a plasticizer; and a pore-forming agent selected from the group consisting of hydroxypropyl cellulose and hydroxypropyl methylcellulose;
wherein the coating surrounds the core.

In certain embodiments, the invention relates to a controlled-release solid dosage form, consisting essentially of a plurality of mini-tablets, wherein each mini-tablet comprises:
(a) a core, consisting essentially of mesalamine; a diluent; a binder, and a lubricant; and
(b) a coating, consisting essentially of low-viscosity ethyl cellulose; a plasticizer; and a pore-forming agent selected from the group consisting of hydroxypropyl cellulose and hydroxypropyl methylcellulose;
wherein the coating surrounds the core.

In certain embodiments, the invention relates to any one of the aforementioned solid dosage forms, wherein the plasticizer is triethyl citrate.

In certain embodiments, the invention relates to any one of the aforementioned solid dosage forms, wherein the number of mini-tablets is about 30 to about 100.

In certain embodiments, the invention relates to any one of the aforementioned solid dosage forms, wherein the number of mini-tablets is about 50 to about 80.

In certain embodiments, the invention relates to any one of the aforementioned solid dosage forms, wherein the number of mini-tablets is about 60 to about 70.

In certain embodiments, the invention relates to any one of the aforementioned solid dosage forms, wherein the number of mini-tablets is about 64.

In certain embodiments, the invention relates to any one of the aforementioned solid dosage forms, wherein the diameter of the mini-tablets is about 1 mm to about 5 mm.

In certain embodiments, the invention relates to any one of the aforementioned solid dosage forms, wherein the diameter of the mini-tablets is about 1.5 mm, about 2.0 mm, about 2.5 mm, about 3.0 mm, about 3.5 mm, about 4.0 mm, about 4.5 mm, or about 5.0 mm.

In certain embodiments, the invention relates to any one of the aforementioned solid dosage forms, wherein the plurality of mini-tablets all have substantially the same diameters.

In certain embodiments, the invention relates to any one of the aforementioned solid dosage forms, wherein the viscosity of any of the components is within a particular range.

The viscosity of particular components can be measured using methods well known to those of ordinary skill in the art. For example, the viscosity of particular components can be measured using methods described in United States Pharmacopeia (USP) test number 911 for measuring viscosity.

In certain embodiments, the invention relates to any one of the aforementioned solid dosage forms, wherein the viscosity of the low-viscosity ethyl cellulose is less than about 15 cP.

In certain embodiments, the invention relates to any one of the aforementioned solid dosage forms, wherein the viscosity of the low-viscosity ethyl cellulose is less than about 12 cP.

In certain embodiments, the invention relates to any one of the aforementioned solid dosage forms, wherein the viscosity of the low-viscosity ethyl cellulose is less than about 7 cP.

In certain embodiments, the invention relates to any one of the aforementioned solid dosage forms, wherein the viscosity of the low-viscosity ethyl cellulose is greater than about 1 cP.

In certain embodiments, the invention relates to any one of the aforementioned solid dosage forms, wherein the ratio in the coating of the low-viscosity ethyl cellulose to the pore-forming agent is about 7:3 to about 4:6.

In certain embodiments, the invention relates to any one of the aforementioned solid dosage forms, wherein the ratio in the coating of the low-viscosity ethyl cellulose to the pore-forming agent is about 6:4 to about 4:6.

In certain embodiments, the invention relates to any one of the aforementioned solid dosage forms, wherein the ratio in the coating of the low-viscosity ethyl cellulose to the pore-forming agent is about 1:1.

In certain embodiments, the invention relates to any one of the aforementioned solid dosage forms, wherein the pore-forming agent is hydroxypropyl cellulose.

In certain embodiments, the invention relates to any one of the aforementioned solid dosage forms, wherein the pore-forming agent is hydroxypropyl methylcellulose.

In certain embodiments, the invention relates to any one of the aforementioned solid dosage forms, wherein the viscosity of the hydroxypropyl cellulose or hydroxypropyl methylcellulose is about 3 cP to about 15 cP.

In certain embodiments, the invention relates to any one of the aforementioned solid dosage forms, wherein the viscosity of the hydroxypropyl cellulose or hydroxypropyl methylcellulose is about 15 cP.

In certain embodiments, the invention relates to any one of the aforementioned solid dosage forms, wherein the solid dosage form does not comprise an acrylic polymer.

In certain embodiments, the invention relates to any one of the aforementioned solid dosage forms, wherein the coating does not comprise an anionic polymer.

In certain embodiments, the invention relates to any one of the aforementioned solid dosage forms, wherein the core does not comprise a lipophilic material.

In certain embodiments, the invention relates to any one of the aforementioned solid dosage forms, wherein the core does not comprise polyvinylpyrrolidone.

In certain embodiments, the invention relates to any one of the aforementioned solid dosage forms, further comprising a diluent, wherein the diluent is selected from the group consisting of lactose; microcrystalline cellulose; starch; mannitol; sorbitol; dextrose; dibasic calcium phosphate; dicalcium phosphate dihydrate; tricalcium phosphate; calcium phosphate; anhydrous lactose; spray-dried lactose; pregelatinized starch; compressible sugar, hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; and bentonite.

In certain embodiments, the invention relates to any one of the aforementioned solid dosage forms, further comprising a diluent, wherein the diluent is selected from the group consisting of lactose; microcrystalline cellulose; starch; mannitol; sorbitol; dextrose; anhydrous lactose; spray-dried lactose; pregelatinized starch; compressible sugar; hydroxypropylmethylcellulose; sucrose-based diluents; confectioner's sugar; calcium lactate trihydrate; dextrates; hydrolyzed cereal solids; amylose; powdered cellulose; and inositol.

In certain embodiments, the invention relates to any one of the aforementioned solid dosage forms, further comprising a diluent, wherein the diluent is selected from the group consisting of lactose; microcrystalline cellulose; dextrose; anhydrous lactose; spray-dried lactose; sucrose-based diluents; confectioner's sugar; and amylose.

In certain embodiments, the invention relates to any one of the aforementioned solid dosage forms, further comprising a diluent, wherein the diluent is lactose or microcrystalline cellulose. In certain embodiments, the solid dosage form comprises lactose. In certain embodiments, the solid dosage form comprises microcrystalline cellulose.

In certain embodiments, the invention relates to any one of the aforementioned solid dosage forms, further comprising a binder, wherein the binder is selected from the group consisting of alginic acid and salts thereof; cellulose derivatives such as carboxymethylcellulose, methylcellulose, hydroxypropylmethylcellulose, hydroxyethylcellulose, hydroxypropylcellulose, ethylcellulose, and microcrystalline cellulose; microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth; dextrin; a sugar, such as sucrose, glucose, dextrose, molasses, mannitol, sorbitol, xylitol, and lactose; a natural or synthetic gum such as acacia, tragacanth, ghatti gum, mucilage of isapol husks, polyvinylpyrrolidone, larch arabogalactan, polyethylene glycol, and sodium alginate.

In certain embodiments, the invention relates to any one of the aforementioned solid dosage forms, further comprising a binder, wherein the binder is selected from the group consisting of cellulose derivatives such as carboxymethylcellulose, methylcellulose, hydroxypropylmethylcellulose, hydroxyethylcellulose, hydroxypropylcellulose, ethylcellulose, and microcrystalline cellulose; microcrystalline dextrose; amylose; polysaccharide acids; starch; and dextrin.

In certain embodiments, the invention relates to any one of the aforementioned solid dosage forms, further comprising a binder, wherein the binder is selected from the group consisting of cellulose derivatives such as carboxymethylcellulose, methylcellulose, hydroxypropylmethylcellulose, hydroxyethylcellulose, hydroxypropylcellulose, ethylcellulose, and microcrystalline cellulose.

In certain embodiments, the invention relates to any one of the aforementioned solid dosage forms, further comprising a binder, wherein the binder is hydroxypropyl cellulose.

In certain embodiments, the invention relates to any one of the aforementioned solid dosage forms, wherein the lubricant is selected from the group consisting of stearic acid; calcium hydroxide; talc; mineral oil; hydrogenated vegetable oil, such as hydrogenated soybean oil; higher fatty acids and their alkali-metal and alkaline earth metal salts, such as aluminum, sodium, calcium, magnesium, or zinc stearates; glycerol; boric acid; sodium acetate; leucine; polyethylene glycol or methoxypolyethylene glycol; sodium oleate; glyceryl behenate; glyceryl palmitostearate; colloidal silica; a starch, such as corn starch; silicone oil; sodium stearyl fumarate; surfactants; magnesium lauryl sulfate; sodium lauryl sulfate; sodium benzoate; and sodium chloride.

In certain embodiments, the invention relates to any one of the aforementioned solid dosage forms, wherein the lubricant is selected from the group consisting of stearic acid; higher fatty acids and their alkali-metal and alkaline earth metal salts, such as aluminum, sodium, calcium, magnesium, or zinc stearates; sodium oleate; sodium stearyl fumarate; magnesium lauryl sulfate; and sodium lauryl sulfate.

In certain embodiments, the invention relates to any one of the aforementioned solid dosage forms, wherein the lubricant is selected from the group consisting of stearic acid; higher fatty acids and their alkali-metal and alkaline earth metal salts, such as aluminum, sodium, calcium, magnesium, or zinc stearates.

In certain embodiments, the invention relates to any one of the aforementioned solid dosage forms, wherein the lubricant is magnesium stearate.

In certain embodiments, the invention relates to any one of the aforementioned solid dosage forms, wherein the weight percentage of the mesalamine is about 40% to about 90% based on the weight of the core. In certain embodiments, the invention relates to any one of the aforementioned solid dosage forms, wherein the weight percentage of the mesalamine is about 75% to about 85% based on the weight of the core. In certain embodiments, the invention relates to any one of the aforementioned solid dosage forms, wherein the weight percentage of the mesalamine is about 40%, about 45%, about 50%, about 55%, about 60%, about 65%, about 70%, about 75%, about 80%, about 85%, or about 90% based on the weight of the core.

In certain embodiments, the invention relates to any one of the aforementioned solid dosage forms, wherein the weight percentage of the mesalamine is about 80% based on the weight of the core.

In certain embodiments, the invention relates to any one of the aforementioned solid dosage forms, wherein the weight percentage of the mesalamine is about 40% to about 90% by weight of the mini-tablet.

In certain embodiments, the invention relates to any one of the aforementioned solid dosage forms, wherein the weight percentage of the mesalamine is about 40%, about 45%, about 50%, about 55%, about 60%, about 65%, about 70%, about 75%, about 80%, about 85%, or about 90% by weight of the mini-tablet.

In certain embodiments, the invention relates to any one of the aforementioned solid dosage forms, further comprising a diluent, wherein the weight percentage of the diluent is about 10% to about 40% based on the weight of the core.

In certain embodiments, the invention relates to any one of the aforementioned solid dosage forms, further comprising a diluent, wherein the weight percentage of the diluent is about 10% to about 25% based on the weight of the core.

In certain embodiments, the invention relates to any one of the aforementioned solid dosage forms, further comprising a diluent, wherein the weight percentage of the diluent is about 10% to about 20% based on the weight of the core.

In certain embodiments, the invention relates to any one of the aforementioned solid dosage forms, further comprising a diluent, wherein the weight percentage of the diluent is about 10%, about 11%, about 12%, about 13%, about 14%, about 15%, about 16%, about 17%, about 18%, about 19%, or about 20% based on the weight of the core.

In certain embodiments, the invention relates to any one of the aforementioned solid dosage forms, further comprising a binder, wherein the weight percentage of the binder is about 1% to about 10% based on the weight of the core.

In certain embodiments, the invention relates to any one of the aforementioned solid dosage forms, further comprising a binder, wherein the weight percentage of the binder is about 1% to about 5% based on the weight of the core.

In certain embodiments, the invention relates to any one of the aforementioned solid dosage forms, further comprising a binder, wherein the weight percentage of the binder is about 1%, about 2%, about 3%, about 4%, or about 5% based on the weight of the core.

In certain embodiments, the invention relates to any one of the aforementioned solid dosage forms, further comprising a lubricant, wherein the weight percentage of the lubricant is about 0.5% to about 5% based on the weight of the core.

In certain embodiments, the invention relates to any one of the aforementioned solid dosage forms, further comprising a lubricant, wherein the weight percentage of the lubricant is about 0.5% to about 3% based on the weight of the core.

In certain embodiments, the invention relates to any one of the aforementioned solid dosage forms, further comprising a lubricant, wherein the weight percentage of the lubricant is about 0.5% to about 1% based on the weight of the core.

In certain embodiments, the invention relates to any one of the aforementioned solid dosage forms, further comprising a lubricant, wherein the weight percentage of the lubricant is about 0.5%, about 0.75%, about 1%, about 2%, about 3%, about 4%, or about 5% based on the weight of the core.

In certain embodiments, the invention relates to any one of the aforementioned solid dosage forms, wherein the weight percentage of the coating is about 1% to about 10% based on the weight of the mini-tablet. In certain embodiments, the invention relates to any one of the aforementioned solid dosage forms, wherein the weight percentage of the coating is about 9%, about 8%, about 7%, about 6%, about 5%, about 4%, about 3%, about 2%, or about 1% based on the weight of the mini-tablet.

In certain embodiments, the invention relates to any one of the aforementioned solid dosage forms, wherein the weight percentage of the coating is about 3% based on the weight of the mini-tablet.

In certain embodiments, the invention relates to any one of the aforementioned solid dosage forms, wherein the weight percentage of the coating is about 2% based on the weight of the mini-tablet.

In certain embodiments, the invention relates to any one of the aforementioned solid dosage forms, wherein the weight percentage of the coating is about 1% based on the weight of the mini-tablet.

In certain embodiments, the invention relates to any one of the aforementioned solid dosage forms, wherein the solid dosage form is a capsule.

In certain embodiments, the invention relates to any one of the aforementioned solid dosage forms, wherein the solid dosage form is a capsule; and the capsule comprises the plurality of mini-tablets.

In certain embodiments, the invention relates to any one of the aforementioned solid dosage forms, wherein the total amount of mesalamine is about 200 mg to about 1,000 mg.

In certain embodiments, the invention relates to any one of the aforementioned solid dosage forms, wherein the total amount of mesalamine is about 250 mg, about 375 mg, about 400 mg, about 500 mg, or about 800 mg.

In certain embodiments, the invention relates to any one of the aforementioned solid dosage forms, wherein the total amount of mesalamine is about 250 mg.

In certain embodiments, the invention relates to any one of the aforementioned solid dosage forms, wherein the total amount of mesalamine is about 375 mg.

In certain embodiments, the invention relates to any one of the aforementioned solid dosage forms, wherein the total amount of mesalamine is about 400 mg.

In certain embodiments, the invention relates to any one of the aforementioned solid dosage forms, wherein the total amount of mesalamine is about 500 mg.

In certain embodiments, the invention relates to any one of the aforementioned solid dosage forms, wherein the total amount of mesalamine is about 800 mg.

In certain embodiments, the invention relates to any one of the aforementioned solid dosage forms, wherein the mini-tablets do not comprise wax.

In certain embodiments, the invention relates to any one of the aforementioned solid dosage forms, wherein the core is substantially soluble in a liquid with pH from about 1 to about 14, from about 1 to about 7 and from 1 to about 5 at a temperature of about 20° C. to about 40° C.

In certain embodiments, the invention relates to any one of the aforementioned solid dosage forms, wherein the pore-forming agent is substantially soluble in a liquid with pH from about 1 to about 5 at a temperature of about 20° C. to about 40° C.

In certain embodiments, the invention relates to any one of the aforementioned solid dosage forms, wherein the diluent is substantially soluble in a liquid with pH from about 1 to about 5 at a temperature of about 20° C. to about 40° C.

In certain embodiments, the invention relates to any one of the aforementioned solid dosage forms, wherein one or more pore-forming agents comprising the coating is substantially soluble in a liquid with pH from about 1 to about 14, from about 1 to about 7 and from 1 to about 5 at a temperature of about 20° C. to about 40° C.

In certain embodiments, the invention relates to any one of the aforementioned solid dosage forms, wherein the core is substantially soluble in gastric juice.

In certain embodiments, the invention relates to any one of the aforementioned solid dosage forms, wherein the pore-forming agent is substantially soluble in gastric juice.

In certain embodiments, the invention relates to any one of the aforementioned solid dosage forms, wherein the diluent is substantially soluble in gastric juice.

In certain embodiments, the invention relates to any one of the aforementioned solid dosage forms, wherein the pore-forming agent comprising the coating is substantially soluble in gastric juice.

In certain embodiments, the invention relates to any one of the aforementioned solid dosage forms, wherein upon contact with gastric juice the mesalamine is substantially immediately released from the core.

In certain embodiments, the invention relates to any one of the aforementioned solid dosage forms, wherein controlled-release of mesalamine from the mini-tablets is substantially controlled by the coating.

In certain embodiments, the invention relates to any one of the aforementioned solid dosage forms, wherein the dissolution profile of the mesalamine in about 900 mL of about 0.05 M phosphate buffer at about pH 7.5 at about 37° C., with paddles rotating at about 100 rpm, is: at about 1 h, between about 5% and about 25%; at about 2 h, between about 30% and about 50%; at about 4 h, between about 60% and about 90%; and at about 8 h, between about 85% and 100%.

In certain embodiments, the invention relates to any one of the aforementioned solid dosage forms, wherein the dissolution profile of the mesalamine in about 900 mL of about 0.05 M phosphate buffer at about pH 6 at about 37° C., with paddles rotating at about 100 rpm, is: at about 1 h, at least about 5%; at about 2 h, at least about 10%; at about 4 h, at least about 20%; and at about 8 h, at least about 50%.

In certain embodiments, the invention relates to any one of the aforementioned solid dosage forms, wherein the dissolution profile of the mesalamine in about 900 mL of about 0.05 M phosphate buffer at about pH 1.2 at about 37° C., with paddles rotating at about 100 rpm, is: at about 1 h, at least about 10%; at about 2 h, at least about 25%; at about 4 h, at least about 50%; and at about 8 h, at least about 80%.

In certain embodiments, the invention relates to any one of the aforementioned solid dosage forms, wherein the failure of the coating on a mini-tablet does not substantially affect the dissolution rate of the mesalamine.

In certain embodiments, the invention relates to a controlled-release solid dosage form, comprising:
  (a) mesalamine in an amount effective for treating inflammatory bowel disease; and
  (b) means for topically delivering in the gastrointestinal tract the effective amount of mesalamine.

In certain embodiments, the invention relates to a controlled-release solid dosage form, consisting essentially of:
  (a) mesalamine in an amount effective for treating inflammatory bowel disease; and
  (b) means for topically delivering in the gastrointestinal tract the effective amount of mesalamine.

In certain embodiments, the invention relates to a controlled-release solid dosage form, comprising:
  (a) mesalamine in an amount effective for inducing remission of inflammatory bowel disease; and
  (b) means for topically delivering in the gastrointestinal tract the effective amount of mesalamine.

In certain embodiments, the invention relates to a controlled-release solid dosage form, consisting essentially of:
  (a) mesalamine in an amount effective for inducing remission of inflammatory bowel disease; and
  (b) means for topically delivering in the gastrointestinal tract the effective amount of mesalamine.

In certain embodiments, the invention relates to a controlled-release solid dosage form, comprising:
  (a) mesalamine in an amount effective for maintaining remission of inflammatory bowel disease; and
  (b) means for topically delivering in the gastrointestinal tract the effective amount of mesalamine.

In certain embodiments, the invention relates to a controlled-release solid dosage form, consisting essentially of:
  (a) mesalamine in an amount effective for maintaining remission of inflammatory bowel disease; and
  (b) means for topically delivering in the gastrointestinal tract the effective amount of mesalamine.

In certain embodiments, the invention relates to a controlled-release solid dosage form, comprising a plurality of mini-tablets, wherein each mini-tablet comprises:

(a) a core, comprising mesalamine in about 80% by weight of the core; lactose in about 16% by weight of the core; hydroxypropyl cellulose in about 3% by weight of the core; and a lubricant in about 1% by weight of the core; and (b) a coating, comprising low-viscosity ethyl cellulose; a pore-forming agent; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; microcrystalline cellulose in about 16% by weight of the core; hydroxypropyl cellulose in about 3% by weight of the core; and a lubricant in about 1% by weight of the core; and (b) a coating, comprising low-viscosity ethyl cellulose; a pore-forming agent; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; lactose in about 16% by weight of the core; hydroxypropyl cellulose in about 3% by weight of the core; and a lubricant in about 1% by weight of the core; and (b) a coating, comprising low-viscosity ethyl cellulose; a pore-forming agent, wherein said pore-forming agent is selected from the group consisting of hydroxypropyl cellulose and hydroxypropylmethyl cellulose; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; lactose in about 16% by weight of the core; hydroxypropyl cellulose in about 3% by weight of the core; and a lubricant in about 1% by weight of the core; and (b) a coating, comprising low-viscosity ethyl cellulose; hydroxypropyl cellulose; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; lactose in about 16% by weight of the core; hydroxypropyl cellulose in about 3% by weight of the core; and a lubricant in about 1% by weight of the core; and (b) a coating, comprising low-viscosity ethyl cellulose; hydroxypropylmethyl cellulose; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; microcrystalline cellulose in about 16% by weight of the core; hydroxypropyl cellulose in about 3% by weight of the core; and a lubricant in about 1% by weight of the core; and (b) a coating, comprising low-viscosity ethyl cellulose; a pore-forming agent, wherein said pore-forming agent is selected from the group consisting of hydroxypropyl cellulose and hydroxypropylmethyl cellulose; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; microcrystalline cellulose in about 16% by weight of the core; hydroxypropyl cellulose in about 3% by weight of the core; and a lubricant in about 1% by weight of the core; and (b) a coating, comprising low-viscosity ethyl cellulose; hydroxypropyl cellulose; and triethyl citrate;

wherein the coating surrounds the core; and the coating comprises from about 1% to about 6% by weight of the mini-tablet.

In certain embodiments, the invention relates to a controlled-release solid dosage form, comprising a plurality of mini-tablets, wherein each mini-tablet comprises:

(a) a core, comprising mesalamine in about 80% by weight of the core; microcrystalline cellulose in about 16% by weight of the core; hydroxypropyl cellulose in about 3% by weight of the core; and a lubricant in about 1% by weight of the core; and (b) a coating, comprising low-viscosity ethyl cellulose; hydroxypropylmethyl cellulose; and triethyl citrate;

wherein the coating surrounds the core; and the coating comprises from about 1% to about 6% by weight of the mini-tablet.

In certain embodiments, the invention relates to any one of the aforementioned solid dosage forms, wherein the solid dosage form is an oral solid dosage form.

In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-t}$ of greater than about 700, greater than about 800, greater than about 900, greater than about 1000, greater than about 1100, greater than about 1200, greater than about 1300, greater than about 1400, greater than about 1500, greater than about 1600, greater than about 1700, greater than about 1800, greater than about 1900, greater than about 2000, greater than about 2500, greater than about 3000, greater than about 3500, greater than about 4000, greater than about 4500, greater than about 5000, greater than about 5500, greater than about 6000, greater than about 6500, greater than about 7000, greater than about 7500, greater than about 8000, greater than about 8500, greater than about 9000, greater than about 9500, greater than about 10000, greater than about 10500, or greater than about 11000 (ng)(h)/mL. In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-t}$ of about 700 to about 15000 (ng)(h)/mL. In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-t}$ of about 700, about 800, about 900, about 1000, about 1100, about 1200, about 1300, about 1400, about 1500, about 1600, about 1700, about 1800, about 1900, about 2000, about 2500, about 3000, about 3500, about 4000, about 4500, about 5000, about 5500, about 6000, about 6500, about 7000, about 7500, about 8000, about 8500, about 9000, about 9500, about 10000, about 10500, about 11000, about 11500, about 12000, about 12500, about 13000, about 13500, or about 14000 (ng)(h)/mL. In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-t}$ of about 11132±139 (ng)(h)/mL. In certain embodiments, the $AUC_{0-t}$ is calculated as described in Example 23. In certain embodiments, the $AUC_{0-t}$ is a geometric mean.

In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-inf}$ of greater than about 700, greater than about 800, greater than about 900, greater than about 1000, greater than about 1100, greater than about 1200, greater than about 1300, greater than about 1400, greater than about 1500, greater than about 1600, greater than about 1700, greater than about 1800, greater than about 1900, greater than about 2000, greater than about 2500, greater than about 3000, greater than about 3500, greater than about 4000, greater than about 4500, greater than about 5000, greater than about 5500, greater than about 6000, greater than about 6500, greater than about 7000, greater than about 7500, greater than about 8000, greater than about 8500, greater than about 9000, greater than about 9500, greater than about 10000, greater than about 10500, greater than about 11000, greater than about 11500, greater than about 12000, greater than about 12500, greater than about 13000, or greater than about 13500 (ng)(h)/mL. In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-inf}$ of about 700 to about 18000 (ng)(h)/mL. In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-t}$ of about 700, about 800, about 900, about 1000, about 1100, about 1200, about 1300, about 1400, about 1500, about 1600, about 1700, about 1800, about 1900, about 2000, about 2500, about 3000, about 3500, about 4000, about 4500, about 5000, about 5500, about 6000, about 6500, about 7000, about 7500, about 8000, about 8500, about 9000, about 9500, about 10000, about 10500, about 11000, about 11500, about 12000, about 12500, about 13000, about 13500, about 14000, about 14500, about 15000, about 15500, about 16000, about 16500, about 17000, about 17500, or about 18000 (ng)(h)/mL. In certain embodiments, the invention relates to any one of the aforementioned solid dosage forms, wherein the solid dosage form comprises about 500 mg of mesalamine; and oral administration of two of the solid dosage forms to a healthy adult human results in an $AUC_{0-inf}$ of about 13741±118 (ng)(h)/mL. In certain embodiments, the $AUC_{0-inf}$ is calculated as described in Example 23. In certain embodiments, the $AUC_{0-inf}$ is a geometric mean.

In certain embodiments, the invention relates to any one of the aforementioned solid dosage forms, wherein the solid dosage form comprises about 500 mg of mesalamine; and oral administration of two of the solid dosage forms to a healthy adult human results in a $C_{max}$ of greater than about 200, greater than about 300, greater than about 400, greater than about 500, greater than about 600, greater than about 700, greater than about 800, greater than about 900, greater than about 1000, greater than about 1100, greater than about 1200, greater than about 1300, greater than about 1400, greater than about 1500, greater than about 1600, greater than about 1700, greater than about 1800, greater than about 1900, greater than about 2000, greater than about 2500, greater than about 3000, greater than about 3500, greater than about 4000, or greater than about 4500 ng/mL. In certain embodiments, the invention relates to any one of the aforementioned solid dosage forms, wherein the solid dosage form comprises about 500 mg of mesalamine; and oral administration of two of the solid dosage forms to a healthy adult human results in a $C_{max}$ of about 300 to about 7500 ng/mL. In certain embodiments, the invention relates to any one of the aforementioned solid dosage forms, wherein the solid dosage form comprises about 500 mg of mesalamine; and oral administration of two of the solid dosage forms to a healthy adult human results in a $C_{max}$ of about 300, about 400, about 500, about 600, about 700, about 800, about 900, about 1000, about 1100, about 1200, about 1300, about 1400, about 1500, about 1600, about 1700, about 1800, about 1900, about 2000, about 2500, about 3000, about 3500, about 4000, about 4500, about 5000, about 5500, about 6000, about 6500, about 7000, or about 7500 ng/mL. In certain embodiments, the invention relates to any one of the aforementioned solid dosage forms, wherein the solid dosage form comprises about 500 mg of mesalamine; and oral administration of two of the solid dosage forms to a healthy adult human results in a $C_{max}$ of about 4901±207 ng/mL. In certain embodiments, the $C_{max}$ is calculated as described in Example 23. In certain embodiments, the $C_{max}$ is a geometric mean.

In certain embodiments, the invention relates to any one of the aforementioned solid dosage forms, wherein the solid dosage form comprises about 500 mg of mesalamine; and oral administration of two of the solid dosage forms to a healthy adult human results in a $t_{max}$ of greater than about 5, greater than about 5.5, or greater than about 6 h. In certain embodiments, the invention relates to any one of the aforementioned solid dosage forms, wherein the solid dosage form comprises about 500 mg of mesalamine; and oral administration of two of the solid dosage forms to a healthy adult human results in a $t_{max}$ of less than about 20, less than about 19, less than about 18, less than about 17, less than about 16, less than about 15, less than about 14, less than about 13, less than about 12, less than about 11, or less than about 10 hours (h). In certain embodiments, the invention relates to any one of the aforementioned solid dosage forms, wherein the solid dosage form comprises about 500 mg of mesalamine; and oral administration of two of the solid dosage forms to a healthy adult human results in a $t_{max}$ of about 2 to about 9, from about 3 to about 9, from about 4 to about 9, from about 5 to about 9, from about 6 to about 9, from about 7 to about 9, or from about 8 to about 9 h. In certain embodiments, the invention relates to any one of the aforementioned solid dosage forms, wherein the solid dosage form comprises about 500 mg of mesalamine; and oral administration of two of the solid dosage forms to a healthy adult human results in a $t_{max}$ of about 5, about 5.5, about 6, about 6.5, about 7, about 7.5, or about 8 h. In certain embodiments, the invention relates to any one of the aforementioned solid dosage forms, wherein the solid dosage form comprises about 500 mg of mesalamine; and oral administration of two of the solid dosage forms to a healthy adult human results in a median $t_{max}$ of about 6 h. In certain embodiments, the $t_{max}$ is calculated as described in Example 23. In certain embodiments, the $t_{max}$ is a median.

In certain embodiments, the invention relates to any one of the aforementioned solid dosage forms, wherein the solid dosage form comprises about 500 mg of mesalamine; and oral administration of two of the solid dosage forms to a healthy adult human results in a tin of less than about 7.0, less than about 6.0, less than about 5.0, or less than about 4.0 hours (h). In certain embodiments, the invention relates to any one of the aforementioned solid dosage forms, wherein the solid dosage form comprises about 500 mg of mesalamine; and oral administration of two of the solid dosage forms to a healthy adult human results in a tin of about 0.5 to about 7.0 h. In certain embodiments, the invention relates to any one of the aforementioned solid dosage forms, wherein the solid dosage form comprises about 500 mg of mesalamine; and oral administration of two of the solid dosage forms to a healthy adult human results in a tin of about 0.5, about 1, about 1.5, about 2, about 2.5, about 3, about 3.5, about 4, about 4.5, about 5, about 5.5, about 6, about 6.5, or about 7 h. In certain embodiments, the invention relates to any one of the aforementioned solid dosage forms, wherein the solid dosage form comprises about 500 mg of mesalamine; and oral administration of two of the solid dosage forms to a healthy adult human results in a $t_{1/2}$ of about 3.60±3.44 h. In certain embodiments, the $t_{1/2}$ is calculated as described in Example 23. In certain embodiments, the tin is an arithmetic mean.

In certain embodiments, the invention relates to any one of the aforementioned solid dosage forms, wherein the solid dosage form comprises about 500 mg of mesalamine; and oral administration of two of the solid dosage forms to a healthy adult human results in a ratio of $AUC_{0-t}/AUC_{0-inf}$ of greater than about 98% or greater than about 99%. In certain embodiments, the invention relates to any one of the aforementioned solid dosage forms, wherein the solid dosage form comprises about 500 mg of mesalamine; and oral administration of two of the solid dosage forms to a healthy adult human results in a ratio of $AUC_{0-t}/AUC_{0-inf}$ of about 98.0% to about 99.9%. In certain embodiments, the invention relates to any one of the aforementioned solid dosage forms, wherein the solid dosage form comprises about 500 mg of mesalamine; and oral administration of two of the solid dosage forms to a healthy adult human results in a ratio of $AUC_{0-t}/AUC_{0-inf}$ of about 98.0%, about 98.2%, about 98.4%, about 98.6%, about 98.8%, about 99.0%, about 99.2%, about 99.4%, about 99.6%, or about 99.8%. In certain embodiments, the invention relates to any one of the aforementioned solid dosage forms, wherein the solid dosage form comprises about 500 mg of mesalamine; and oral administration of two of the solid dosage forms to a healthy adult human results in a ratio of $AUC_{0-t}/AUC_{0-inf}$ of 99.7±0.647%. In certain embodiments, the ratio of $AUC_{0-t}/AUC_{0-inf}$ is calculated as described in Example 23. In certain embodiments, the ratio of $AUC_{0-t}/AUC_{0-inf}$ is an arithmetic mean.

In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $AUC_{0-t}$ values of about 15 to about 25, about 16 to about 25, about 17 to about 25, about 17 to about 20, about 18 to about 20, or about 19 to about 20. In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $AUC_{0-t}$ values of about 15, about 16, about 17, about 18, about 19, about 20, about 21, about 22, about 23, about 24, or about 25. In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $AUC_{0-t}$ values of about 19.

In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $AUC_{0-inf}$ values of about 20 to about 30, about 22 to about 30, about 23 to about 28, about 23 to about 25, or about 24 to about 25. In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $AUC_{0-inf}$ values of about 20, about 21, about 22, about 23, about 24, about 25, about 26, about 27, about 28, about 29, or about 30. In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $AUC_{0-inf}$ values of about 24.6 or about 25.

In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $C_{max}$ values of about 25 to about 35, about 26 to about 35, about 27 to about 35 about 28 to about 35, about 28 to about 34, about 28 to about 33, about 29 to about 34, about 29 to about 33, about 30 to about 33, about 30 to about 32, or about 31 to about 32. In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $C_{max}$ values of about 25, about 26, about 27, about 28, about 29, about 30, about 31, about 32, about 33, about 34, or about 35. In certain embodiments, the invention relates to any one of the aforementioned solid dosage forms, wherein the solid dosage form comprises about 500 mg of mesalamine; and oral administration of two of the solid dosage forms to a healthy adult human as compared to administration of 1000 mg of Treatment B results in a ratio of $C_{max}$ values of about 31.6 or about 32.

In one embodiment, the invention relates to any one of the above-mentioned solid dosage forms for use in the treatment of inflammatory bowel disease.

In one embodiment, the invention relates to any one of the above-mentioned solid dosage forms for use in inducing remission of inflammatory bowel disease.

In one embodiment, the invention relates to any one of the above-mentioned solid dosage forms for use in maintaining remission of inflammatory bowel disease.

In certain embodiments, the invention relates to a method of treating inflammatory bowel disease, comprising the step of orally administering to a mammal in need thereof a therapeutically effective amount of any one of the aforementioned solid dosage forms.

In certain embodiments, the invention relates to a method of inducing remission of inflammatory bowel disease, comprising the step of orally administering to a mammal in need thereof a therapeutically effective amount of any one of the aforementioned solid dosage forms. In certain embodiments, "remission" (clinical or endoscopic) is defined as a Ulcerative Colitis Disease Activity Index (UCDAI) score of ≤1, with scores of 0 for both rectal bleeding and stool frequency, normal mucosa (no friability) on endoscopy, and a ≥1 point reduction in the Endoscopic Index (EI) score. The UCDAI is explained in more detail in Sutherland et al. Gastroenterology 1987, 92, 1894-98, and Walmsley, et al. Gut 1998, 43, 29-32. Alternatively, remission is defined as complete resolution of symptoms plus improvement of endoscopic endpoints (e.g., a "1" score for one of the endoscopic components (mucosal vascular pattern, erythema, granularity, or friability), and "0" for the others). An alternative or additional measure is Sigmoidoscopic Index (SI)—an objective measure of disease activity rated by a standard 15-point scale that includes mucosal vascular pattern, erythema, friability, granularity/ulcerations, and mucopus as an improvement over baseline. Secondary efficacy parameters that also may be indicative of remission include, but are not limited to, reduction in the frequency of trips to the toilet, improved stool consistency, decreased rectal bleeding, decreased abdominal pain/rectal pain, and decreased urgency compared to these measures prior the administration of a solid oral dosage form according to the present invention.

In certain embodiments, the invention relates to a method of maintaining remission of inflammatory bowel disease, comprising the step of orally administering to a mammal in need thereof a therapeutically effective amount of any one of the aforementioned solid dosage forms.

In certain embodiments, the invention relates to a method, comprising the steps of:

orally administering to a mammal in need thereof a therapeutically effective amount of any one of the aforementioned solid dosage forms for a first period of time; and orally co-administering to the mammal a therapeutically effective amount of a steroid and a therapeutically effective amount of any one of the aforementioned solid dosage forms for a second period of time, thereby inducing remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to a method, comprising the steps of:

orally administering to a mammal in need thereof a therapeutically effective amount of any one of the aforementioned solid dosage forms for a first period of time;

orally co-administering to the mammal a therapeutically effective amount of a steroid and a therapeutically effective amount of any one of the aforementioned solid dosage forms for a second period of time, thereby inducing remission of inflammatory bowel disease; and orally administering to the mammal a therapeutically effective amount of any one of the aforementioned solid dosage forms for a third period of time, thereby maintaining remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to any one of the aforementioned methods, wherein the first period of time is from about 3 weeks to about 9 weeks. In certain embodiments, the invention relates to any one of the aforementioned methods, wherein the first period of time is about 3 weeks, about 4 weeks, about 5 weeks, about 6 weeks, about 7 weeks, about 8 weeks, or about 9 weeks.

In certain embodiments, the invention relates to any one of the aforementioned methods, wherein the second period of time is from about 4 weeks to about 12 weeks. In certain embodiments, the invention relates to any one of the aforementioned methods, wherein the second period of time is about 4 weeks, about 5 weeks, about 6 weeks, about 7 weeks, about 8 weeks, about 9 weeks, about 10 weeks, about 11 weeks, or about 12 weeks.

In certain embodiments, the invention relates to any one of the aforementioned methods, wherein the third period of time is from about 3 weeks to about 9 weeks. In certain embodiments, the invention relates to any one of the aforementioned methods, wherein the third period of time is about 3 weeks, about 4 weeks, about 5 weeks, about 6 weeks, about 7 weeks, about 8 weeks, or about 9 weeks.

In certain embodiments, the invention relates to any one of the aforementioned methods, wherein the steroid and the solid dosage, when administered for the second period of time, effectively induce remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to a method, comprising the steps of:

orally administering to a mammal in need thereof a therapeutically effective amount of a steroid for a fourth period of time, thereby inducing remission of inflammatory bowel disease, and orally administering to the mammal a therapeutically effective amount of any one of the aforementioned solid dosage forms for a fifth period of time, thereby maintaining remission of inflammatory bowel disease.

In certain embodiments, the invention relates to any one of the aforementioned methods, wherein the therapeutically effective amount of the steroid, when administered for the fourth period of time, effectively induces remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to any one of the aforementioned methods, wherein the fourth period of time is from about 4 weeks to about 12 weeks. In certain embodiments, the invention relates to any one of the aforementioned methods, wherein the fourth period of time is about 4 weeks, about 5 weeks, about 6 weeks, about 7 weeks, about 8 weeks, about 9 weeks, about 10 weeks, about 11 weeks, or about 12 weeks.

In certain embodiments, the invention relates to any one of the aforementioned methods, wherein the fifth period of time is from about 3 weeks to about 9 weeks. In certain embodiments, the invention relates to any one of the aforementioned methods, wherein the fifth period of time is about 3 weeks, about 4 weeks, about 5 weeks, about 6 weeks, about 7 weeks, about 8 weeks, or about 9 weeks.

In certain embodiments, the invention relates to a method of maintaining remission of inflammatory bowel disease, comprising the steps of:

orally co-administering to a mammal in need thereof a therapeutically effective amount of a steroid and a therapeutically effective amount of any one of the aforementioned solid dosage forms for a sixth period of time, thereby maintaining remission of inflammatory bowel disease.

In certain embodiments, the invention relates to any one of the aforementioned methods, wherein the sixth period of time is from about 4 weeks to about 12 weeks. In certain embodiments, the invention relates to any one of the aforementioned methods, wherein the sixth period of time is about 4 weeks, about 5 weeks, about 6 weeks, about 7 weeks, about 8 weeks, about 9 weeks, about 10 weeks, about 11 weeks, or about 12 weeks.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to a method of maintaining remission of inflammatory bowel disease, comprising the steps of:

orally administering to a mammal in need thereof a therapeutically effective amount of a steroid for a seventh period of time, thereby maintaining remission of inflammatory bowel disease.

In certain embodiments, the invention relates to any one of the aforementioned methods, wherein the seventh period of time is from about 4 weeks to about 12 weeks. In certain embodiments, the invention relates to any one of the aforementioned methods, wherein the seventh period of time is about 4 weeks, about 5 weeks, about 6 weeks, about 7 weeks, about 8 weeks, about 9 weeks, about 10 weeks, about 11 weeks, or about 12 weeks.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to any one of the aforementioned methods, wherein the inflammatory bowel disease is ulcerative colitis.

In certain embodiments, the invention relates to any one of the aforementioned methods, wherein the inflammatory bowel disease is Crohn's disease.

In certain embodiments, the invention relates to any one of the aforementioned methods, wherein the method is a method of treating or inducing remission of ulcerative colitis; and the ulcerative colitis is mildly active.

In certain embodiments, the invention relates to any one of the aforementioned methods, wherein the method is a method of treating or inducing remission of ulcerative colitis; and the ulcerative colitis is moderately active.

In certain embodiments, the invention relates to any one of the aforementioned methods, wherein the method is a method of maintaining remission of ulcerative colitis; and the ulcerative colitis was mildly active prior to remission.

In certain embodiments, the invention relates to any one of the aforementioned methods, wherein the method is a method of maintaining remission of ulcerative colitis; and the ulcerative colitis was moderately active prior to remission.

In certain embodiments, the invention relates to any one of the aforementioned methods, wherein the mammal is a primate, canine or feline.

In certain embodiments, the invention relates to any one of the aforementioned methods, wherein the mammal is a human.

In certain embodiments, the invention relates to any one of the aforementioned methods, wherein the solid dosage form is administered one, two, three or four times a day.

In certain embodiments, the invention relates to any one of the aforementioned methods, wherein the solid dosage form is administered one time a day.

In certain embodiments, the invention relates to any one of the aforementioned methods, wherein the solid dosage form is administered two times a day.

In certain embodiments, the invention relates to any one of the aforementioned methods, wherein the solid dosage form is administered three times a day.

In certain embodiments, the invention relates to any one of the aforementioned methods, wherein the solid dosage form is administered four times a day.

In certain embodiments, the invention relates to any one of the aforementioned methods, wherein the total daily dose of mesalamine is about 1 g to about 5 g.

In certain embodiments, the invention relates to any one of the aforementioned methods, wherein the total daily dose of mesalamine is about 1.5 g, about 1.6 g, about 2.4 g, or about 4 g.

In certain embodiments, the invention relates to any one of the aforementioned methods, wherein the total daily dose of mesalamine is about 1.5 g.

In certain embodiments, the invention relates to any one of the aforementioned methods, wherein the total daily dose of mesalamine is about 1.6 g.

In certain embodiments, the invention relates to any one of the aforementioned methods, wherein the total daily dose of mesalamine is about 2.4 g.

In certain embodiments, the invention relates to any one of the aforementioned methods, wherein the total daily dose of mesalamine is about 4 g.

In certain embodiments, the invention relates to any one of the aforementioned methods, wherein the solid dosage form is administered four times a day; each solid dosage form comprises about 1 g of mesalamine; and the total daily dose of mesalamine is about 4 g.

In certain embodiments, the invention relates to any one of the aforementioned methods, wherein the mini-tablets pass substantially freely through the pyloric sphincter of the stomach.

In certain embodiments, the invention relates to any one of the aforementioned methods, further comprising the step of co-administering to the mammal in need thereof a therapeutically effective amount of a steroid.

In certain embodiments, the invention relates to any one of the aforementioned methods, wherein the steroid is selected from the group consisting of budesonide, prednisone, dexamethasone, hydrocortisone, methylprednisolone, and prednisolone.

In certain embodiments, the invention relates to any one of the aforementioned methods, wherein the steroid is budesonide.

In certain embodiments, the invention relates to any one of the aforementioned methods, wherein the steroid is budesonide; and the steroid is administered orally.

In certain embodiments, the invention relates to any one of the aforementioned methods, wherein the total daily dose of budesonide is about 3 mg to about 12 mg, or about 6 mg to about 9 mg.

In certain embodiments, the invention relates to any one of the aforementioned methods, wherein the total daily dose of budesonide is about 3 mg, about 6 mg, about 9 mg, or about 12 mg.

In certain embodiments, the invention relates to any one of the aforementioned methods, wherein the total daily dose of budesonide is about 6 mg; and the method is a method of maintaining remission of inflammatory bowel disease.

In certain embodiments, the invention relates to any one of the aforementioned methods, wherein the total daily dose of budesonide is about 6 mg; the method is a method of maintaining remission of inflammatory bowel disease; and the budesonide is administered for about 1 week to about 12 months.

In certain embodiments, the invention relates to any one of the aforementioned methods, wherein the total daily dose of budesonide is about 9 mg.

In certain embodiments, the invention relates to any one of the aforementioned methods, wherein the total daily dose of budesonide is about 9 mg; and the method is a method of inducing remission of inflammatory bowel disease.

In certain embodiments, the invention relates to any one of the aforementioned methods, wherein the total daily dose of budesonide is about 9 mg; the method is a method of inducing remission of inflammatory bowel disease; and the budesonide is administered for about 1 week to about 8 weeks.

In certain embodiments, the invention relates to any one of the aforementioned methods, wherein the steroid is budesonide.

In certain embodiments, the invention relates to any one of the aforementioned methods, wherein the steroid is budesonide; and the budesonide is in the form of an extended release tablet. In certain embodiments, the invention relates to any one of the aforementioned methods, wherein the steroid is budesonide; and the budesonide is in the form of an extended release tablet as described in Example 24.

In certain embodiments, the invention relates to any one of the aforementioned methods, wherein the steroid is budesonide; and the budesonide is in a solid dosage form consisting essentially of budesonide, stearic acid, lecithin, microcrystalline cellulose, hydroxypropylcellulose, lactose monohydrate, silicon dioxide, magnesium stearate, a first acrylic/methacrylic copolymer, a second acrylic/methacrylic copolymer, talc, titanium dioxide, triethylcitrate, and alcohol.

In certain embodiments, the invention relates to any one of the aforementioned methods, wherein the steroid is budesonide; and the budesonide is in a solid dosage form consisting essentially of a tablet core and a coating. In certain embodiments, the budesonide tablet core consists essentially of budesonide, stearic acid, lecithin, microcrystalline cellulose, hydroxypropylcellulose, lactose monohydrate, silicon dioxide, and magnesium stearate. In certain embodiments, the budesonide tablet coating consists essentially of a first acrylic/methacrylic copolymer, a second acrylic/methacrylic copolymer, talc, titanium dioxide, triethylcitrate, and alcohol.

In certain embodiments, the invention relates to any one of the aforementioned methods, wherein the steroid is budesonide; the budesonide is in a solid dosage form consisting essentially of a tablet core and a coating; the budesonide tablet core consists essentially of budesonide, stearic acid, lecithin, microcrystalline cellulose, hydroxypropylcellulose, lactose monohydrate, silicon dioxide, and magnesium stearate; and the budesonide tablet coating consists essentially of a first acrylic/methacrylic copolymer, a second acrylic/methacrylic copolymer, talc, titanium dioxide, triethylcitrate, and alcohol.

In certain embodiments, the invention relates to any one of the aforementioned methods, wherein the steroid is budesonide; the budesonide is in a solid dosage form comprising a tablet core and a coating; the budesonide tablet core comprises about 6 mg budesonide, about 10 mg stearic acid, about 10 mg lecithin, about 156 mg microcrystalline cellulose, about 60 mg hydroxypropylcellulose, about 53 mg lactose monohydrate, about 2 mg silicon dioxide, and about 3 mg magnesium stearate; and the budesonide tablet coating comprises about 8 mg of a first acrylic/methacrylic copolymer, about 8 mg of a second acrylic/methacrylic copolymer, about 7.9 mg of talc, about 4.5 mg titanium dioxide, about 1.6 mg of triethylcitrate, and alcohol.

In certain embodiments, the invention relates to any one of the aforementioned methods, wherein the steroid is budesonide; the budesonide is in a solid dosage form comprising a tablet core and a coating; the budesonide tablet core comprises 9.0 mg budesonide, about 10 mg stearic acid, about 10 mg lecithin, about 156 mg microcrystalline cellulose, about 60 mg hydroxypropylcellulose, about 50 mg lactose monohydrate, about 2 mg silicon dioxide, and about 3 mg magnesium stearate; and the tablet core is coated with a coating comprising about 8 mg of a first acrylic/methacrylic copolymer, about 8 mg of a second acrylic/methacrylic copolymer, about 7.9 mg of talc, about 4.5 mg titanium dioxide, about 1.6 mg of triethylcitrate, and alcohol.

In certain embodiments, the invention relates to any one of the aforementioned methods, wherein the steroid is budesonide; the budesonide is in a solid dosage form consisting essentially of a tablet core and a coating; the budesonide tablet core consists essentially of about 6.0 mg budesonide, about 10.0 mg stearic acid, about 10.0 mg lecithin, about 156.0 mg microcrystalline cellulose, about 60.0 mg hydroxypropylcellulose, about 53.0 mg lactose monohydrate, about 2.0 mg silicon dioxide, and about 3.0 mg magnesium stearate; and the budesonide tablet coating consists essentially of about 8.0 mg of a first acrylic/methacrylic copolymer, about 8.0 mg of a second acrylic/methacrylic copolymer, about 7.9 mg of talc, about 4.5 mg titanium dioxide, about 1.6 mg of triethylcitrate, and alcohol.

In certain embodiments, the invention relates to any one of the aforementioned methods, wherein the steroid is budesonide; and the budesonide is in a solid dosage form described in U.S. Pat. Nos. 7,431,943, 7,410,651, RE43,799, or 8,293,273, or U.S. Patent Application Publication No. US 2012/0021052 A1 (the contents of all of which are hereby incorporated by reference in their entireties).

In certain embodiments, the invention relates to any one of the aforementioned methods, wherein the steroid is budesonide; the budesonide is in a solid dosage form; and the budesonide solid dosage form is UCERIS™ budesonide extended release tablets.

In one embodiment, the invention relates to any one of the above-mentioned methods, wherein the method is used for a period of treatment. In one embodiment, the invention relates to any one of the above-mentioned methods, wherein the period of treatment is about 1 week to about 36 months. In one embodiment, the invention relates to any one of the above-mentioned methods, wherein the period of treatment is about 1, 2, 3, 4, 5, 6, 7, or 8 weeks. In one embodiment, the invention relates to any one of the above-mentioned methods, wherein the period of treatment is about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months.

In one embodiment, the invention relates to the use of mesalamine in the manufacture of a medicament for the treatment of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In one embodiment, the invention relates to the use of mesalamine in the manufacture of a medicament for inducing remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In one embodiment, the invention relates to the use of mesalamine in the manufacture of a medicament for maintaining remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In one embodiment, the invention relates to the use of mesalamine in the manufacture of a solid dosage form for the treatment of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In one embodiment, the invention relates to the use of mesalamine in the manufacture of a solid dosage form for inducing remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In one embodiment, the invention relates to the use of mesalamine in the manufacture of a solid dosage form for maintaining remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

The following examples provide illustrative methods for making and testing the effectiveness of exemplary multiparticulate dosage forms. These examples are provided for illustrative purposes only and not to limit the scope of the claims provided herein. All of the methods disclosed and claimed herein can be made and executed without undue experimentation in light of the present disclosure. It will be apparent to those of ordinary skill in the art that variations may be applied to the methods and in the steps or in the sequence of steps of the method described herein without departing from the concept, spirit and scope of the claims. All such similar substitutes and modifications apparent to those of ordinary skill in the art are deemed to be within the spirit, scope and concept of the appended claims.

While preferred embodiments of the present invention have been shown and described herein, it will be obvious to those of ordinary skill in the art that such embodiments are provided by way of example only. Numerous variations, changes, and substitutions will now occur to those of ordinary skill in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLE 1

General Process for Preparing Uncoated Mini-tablet Cores

An exemplary general process for preparing uncoated mini-tablet cores according to the present invention is provided below. This example is provided for illustrative purposes only and is not meant to limit the scope of the claims provided herein. All of the methods disclosed and claimed herein can be made and executed without undue experimentation in light of the present disclosure. It will be apparent to those of ordinary skill in the art that variations may be applied to the methods and in the steps or in the sequence of steps of the method described herein without departing from the concept, spirit and scope of the claims. All such similar substitutes and modifications apparent to those of ordinary skill in the art are deemed to be within the spirit, scope and concept of the appended claims.

Mesalamine USP, hydroxypropyl cellulose NF (Klucel EXF) and microcrystalline cellulose NF (PH102) or lactose are mixed in a granulator for 2 minutes with an impeller speed of 500 RPM and a chopper speed of 3000 RPM. A 7.5% w/w hydroxypropyl cellulose NF solution in purified water USP is slowly added to the blend while mixing. Additional purified water USP is then added to the blend. The blend is subsequently mixed to complete granulation.

The granules are passed through a coarse screen (#8 or #10 US MESH) and dried in a fluid bed drier at about 60° C. to a final loss-on-drying (LOD) of less 1% to 2%. The dried granules are passed through a #30 US MESH screen and mixed with a lubricant, such as magnesium stearate NP, to form a final blend.

Exemplary mini-tablet cores are prepared from the final blend by feeding the final blend into a Rimek rotary tablet press fitted with multiple tipped punches to produce mini-tablet cores of 2.25 mm in diameter. The resulting mini-tablet cores are compressed at an average weight of approximately 11.3 mg, a thickness of 2.51 mm and an average hardness of 1.67 kp with a friability of nil.

One of ordinary skill in the art will appreciate that mini-tablets cores of different sizes, shapes, and containing more or less mesalamine can be prepared according to the methods described herein as well as those known to those of ordinary skill in the art.

EXAMPLE 2

Pharmaceutical Formulation

Uncoated mini-tablet cores were manufactured to the following formula according to Example 1:

| Component | mg/mini-tablet | % |
|---|---|---|
| Mesalamine, USP | 7.850 | 69.47 |
| Hydroxypropyl Cellulose, NF (Klucel EXF) | 0.336 | 2.98 |
| Microcrystalline Cellulose, NF (PH102) | 3.028 | 26.80 |
| Magnesium Stearate, NF | 0.085 | 0.75 |
| Core Weight: | 11.299 | 100.00 |

EXAMPLE 3

Pharmaceutical Formulation

Uncoated mini-tablet cores were manufactured to the following formula according to Example 1:

| Component | mg/mini-tablet | % |
|---|---|---|
| Mesalamine, USP | 7.801 | 79.60 |
| Hydroxypropyl Cellulose, NF (Klucel EXF) | 0.293 | 2.98 |
| Microcrystalline Cellulose, NF (PH102) | 1.658 | 16.92 |
| Magnesium Stearate, NF | 0.049 | 0.50 |
| Core Weight: | 9.801 | 100.00 |

EXAMPLE 4

Pharmaceutical Formulation

Uncoated mini-tablet cores were manufactured to the following formula according to Example 1:

| Component | mg/mini-tablet | % |
|---|---|---|
| Mesalamine, USP | 7.809 | 79.20 |
| Hydroxypropyl Cellulose, NF (Klucel EXF) | 0.293 | 2.97 |
| Microcrystalline Cellulose, NF (PH102) | 1.659 | 16.83 |
| Magnesium Stearate, NF | 0.099 | 1.00 |
| Core Weight: | 9.860 | 100.00 |

EXAMPLE 5a

Pharmaceutical Formulation

Uncoated mini-tablet cores were manufactured to the following formula according to Example 1:

| Component | mg/mini-tablet | % |
|---|---|---|
| Mesalamine, USP | 7.812 | 79.18 |
| Hydroxypropyl Cellulose, NF (Klucel EXF) | 0.293 | 2.97 |
| Lactose Monohydrate, NF | 1.663 | 16.86 |
| Magnesium Stearate, NF | 0.098 | 0.99 |
| Core Weight: | 9.866 | 100.00 |

EXAMPLE 6

General Process for Coating Mini-tablet Cores

An exemplary process for coating the mini-tablet cores prepared according the present invention, such as those described in Examples 1 to 5 is provided below. This example is provided for illustrative purposes only and is not meant to limit the scope of the claims provided herein. All of the methods disclosed and claimed herein can be made and executed without undue experimentation in light of the present disclosure. It will be apparent to those of ordinary skill in the art that variations may be applied to the methods and in the steps or in the sequence of steps of the method described herein without departing from the concept, spirit and scope of the claims. All such similar substitutes and modifications apparent to those of ordinary skill in the art are deemed to be within the spirit, scope and concept of the appended claims.

An exemplary coating solution is prepared to a batch size of 2 kg with a percent solids content of about 4.5%. Table 6-1 identifies the components of the exemplary coating solution formulation.

TABLE 6-1

| Coating Solution Formulation | | |
|---|---|---|
| Material | % w/w | Weight (g) |
| Ethylcellulose (ECN10) | About 2 | About 40 |
| HPMC (603) | About 2 | About 40 |
| Triethylcitrate | About 0.4 | About 8 |
| Ethanol | About 95 | About 1910 |
| Total | 100.00 | 2000.00 |

Note:
Triethylcitrate is 10% of total polymer content

An exemplary coating process uses a ¼JAU from Spraying Systems spray gun fitted with a 40100 anti-bearding tip and nozzle. Exemplary parameters for an exemplary coating process are identified in Table 6-2.

TABLE 6-2

| Coating pan parameters | |
|---|---|
| Parameter | Setpoint |
| Spray rate | 14-15 g/min |
| Product temperature | 25-30° C. |
| Air volume | 150 cfm |
| Pan speed | 10 rpm |
| Atomization air | 16 psi |

The mini-tablet cores are pre-heated in the pan until they are within the range of 25-30° C. and the coating solution is sprayed on the mini-tablet cores. In order to identify the appropriate weight gain for the desired dissolution profile, tablet samples are taken during the coating process at specified theoretical weight gains. For example, samples can be taken at about 2.6%, about 2.8%, about 3.0%, and about 3.2% weight gains. After a designated weight gain is attained, the inlet temperature is increased to 45° C. and the tablets are dried in the pan for about 30 minutes.

EXAMPLE 7

Pharmaceutical Formulation

Coated mini-tablets are manufactured according to the following formula according to Example 6.

| Component | mg/mini-tablet | % |
|---|---|---|
| Mini-tablet core | 9.836 | 94.52 |
| Ethyl Cellulose, ECN10 | 0.259 | 2.49 |
| Hydroxypropyl Cellulose, Klucel EF, NF | 0.259 | 2.49 |
| Triethyl citrate | 0.052 | 0.50 |
| Coated Weight: | 10.406 | 100.00 |

EXAMPLE 8

Pharmaceutical Formulation

Coated mini-tablets are manufactured according to the following formula according to Example 6.

| Component | mg/mini-tablet | % |
|---|---|---|
| Mini-tablet core | 9.836 | 93.77 |
| Ethyl Cellulose, ECN10 | 0.297 | 2.83 |
| Hydroxypropyl Cellulose, Klucel EF, NF | 0.297 | 2.83 |
| Triethyl citrate | 0.059 | 0.57 |
| Coated Weight: | 10.489 | 100.00 |

EXAMPLE 9

Pharmaceutical Formulation

Coated mini-tablets are manufactured according to the following formula according to Example 6.

| Component | mg/mini-tablet | % |
|---|---|---|
| Mini-tablet core | 9.670 | 96.37 |
| Ethyl Cellulose, ECN10 | 0.166 | 1.65 |
| Hydroxypropyl Cellulose, Klucel EF, NF | 0.166 | 1.65 |
| Triethyl citrate | 0.033 | 0.33 |
| Coated Weight: | 10.035 | 100.00 |

EXAMPLE 10

Pharmaceutical Formulation

Coated mini-tablets are manufactured according to the following formula according to Example 6.

| Component | mg/mini-tablet | % |
|---|---|---|
| Mini-tablet core | 9.670 | 95.34 |
| Ethyl Cellulose, ECN10 | 0.215 | 2.12 |
| Hydroxypropyl Cellulose, Klucel EF, NF | 0.215 | 2.12 |
| Triethyl citrate | 0.043 | 0.42 |
| Coated Weight: | 10.143 | 100.00 |

EXAMPLE 11

Pharmaceutical Formulation

Coated mini-tablets are manufactured according to the following formula according to Example 6.

| Component | mg/mini-tablet | % |
|---|---|---|
| Mini-tablet core | 9.670 | 94.66 |
| Ethyl Cellulose, ECN10 | 0.248 | 2.43 |
| Hydroxypropyl Cellulose, Klucel EF, NF | 0.248 | 2.43 |
| Triethyl citrate | 0.049 | 0.48 |
| Coated Weight: | 10.215 | 100.00 |

EXAMPLE 12

Pharmaceutical Formulation

Coated mini-tablets are manufactured according to the following formula according to Example 6.

| Component | mg/mini-tablet | % |
|---|---|---|
| Mini-tablet core | 9.670 | 97.78 |
| Ethyl Cellulose, ECN10 | 0.100 | 1.01 |
| Hydroxypropyl Methylcellulose, NF | 0.100 | 1.01 |
| Triethyl citrate | 0.020 | 0.20 |
| Coated Weight: | 9.890 | 100.00 |

EXAMPLE 13

Pharmaceutical Formulation

Coated mini-tablets are manufactured according to the following formula according to Example 6.

| Component | mg/mini-tablet | % |
|---|---|---|
| Mini-tablet core | 9.670 | 96.82 |
| Ethyl Cellulose, ECN10 | 0.144 | 1.44 |
| Hydroxypropyl Methylcellulose, NF | 0.145 | 1.45 |
| Triethyl citrate | 0.029 | 0.29 |
| Coated Weight: | 9.988 | 100.00 |

EXAMPLE 14

Pharmaceutical Formulation

Coated mini-tablets are manufactured according to the following formula according to Example 6.

| Component | mg/mini-tablet | % |
|---|---|---|
| Mini-tablet core | 9.670 | 96.49 |
| Ethyl Cellulose, ECN10 | 0.159 | 1.59 |
| Hydroxypropyl Methylcellulose, NF | 0.160 | 1.60 |
| Triethyl citrate | 0.032 | 0.32 |
| Coated Weight: | 10.021 | 100.00 |

EXAMPLE 15

Pharmaceutical Formulation

Coated mini-tablets are manufactured according to the following formula according to Example 6.

| Component | mg/mini-tablet | % |
|---|---|---|
| Mini-tablet core | 9.870 | 96.37 |
| Ethyl Cellulose, ECN10 | | 1.65 |
| Hydroxypropyl Cellulose, Klucel EF, NF | | 1.65 |
| Triethyl citrate | | 0.33 |
| Coated Weight: | 10.105 | 100.00 |

EXAMPLE 16

Pharmaceutical Formulation

Coated mini-tablets are manufactured according to the following formula according to Example 6.

| Component | mg/mini-tablet | % |
|---|---|---|
| Mini-tablet core | 9.870 | 95.34 |
| Ethyl Cellulose, ECN10 | | 2.12 |
| Hydroxypropyl Cellulose, Klucel EF, NF | | 2.12 |
| Triethyl citrate | | 0.42 |
| Coated Weight: | 10.177 | 100.00 |

EXAMPLE 17

Pharmaceutical Formulation

Coated mini-tablets are manufactured according to the following formula according to Example 6.

| Component | mg/mini-tablet | % |
|---|---|---|
| Mini-tablet core | 9.870 | 94.66 |
| Ethyl Cellulose, ECN10 | | 2.43 |
| Hydroxypropyl Cellulose, Klucel EF, NF | | 2.43 |
| Triethyl citrate | | 0.48 |
| Coated Weight: | 10.218 | 100.00 |

EXAMPLE 18a

Pharmaceutical Formulation

Coated mini-tablets are manufactured according to the following formula according to Example 6.

| Component | mg/mini-tablet | % |
|---|---|---|
| Mini-tablet core | 9.870 | 94.66 |
| Ethyl Cellulose, ECN10 | | 2.43 |
| Hydroxypropyl Cellulose, Klucel EF, NF | | 2.43 |
| Triethyl citrate | | 0.48 |
| Coated Weight: | 10.30 | 100.00 |

EXAMPLE 18b

Pharmaceutical Formulation

Coated mini-tablets are manufactured according to the following formula according to Example 6.

| Component | mg/mini-tablet | % |
|---|---|---|
| Mini-tablet core | 9.870 | 94.66 |
| Ethyl Cellulose, ECN10 | | 2.92 |
| Hydroxypropyl Cellulose, Klucel EF, NF | | 1.94 |
| Triethyl citrate | | 0.48 |
| Coated Weight: | 10.30 | 100.00 |

EXAMPLE 18c

Pharmaceutical Formulation

Coated mini-tablets are manufactured according to the following formula according to Example 6.

| Component | mg/mini-tablet | % |
|---|---|---|
| Mini-tablet core | 9.870 | 94.66 |
| Ethyl Cellulose, ECN10 | | 2.92 |
| Hydroxypropyl Methylcellulose, NF | | 1.94 |
| Triethyl citrate | | 0.48 |
| Coated Weight: | 10.30 | 100.00 |

EXAMPLE 18d

Pharmaceutical Formulation

Coated mini-tablets are manufactured according to the following formula according to Example 6.

| Component | mg/mini-tablet | % |
|---|---|---|
| Mini-tablet core | 9.870 | 94.66 |
| Ethyl Cellulose, ECN10 | | 1.94 |
| Hydroxypropyl Cellulose, Klucel EF, NF | | 2.92 |
| Triethyl citrate | | 0.48 |
| Coated Weight: | 10.30 | 100.00 |

EXAMPLE 18e

Pharmaceutical Formulation

Coated mini-tablets are manufactured according to the following formula according to Example 6.

| Component | mg/mini-tablet | % |
|---|---|---|
| Mini-tablet core | 9.870 | 94.66 |
| Ethyl Cellulose, ECN10 | | 1.94 |
| Hydroxypropyl Methylcellulose, NF | | 2.92 |
| Triethyl citrate | | 0.48 |
| Coated Weight: | 10.30 | 100.00 |

EXAMPLE 19

Pharmaceutical Formulation

A pharmaceutical formulation according to the invention was prepared as follows. The identity of the equipment used to prepare the formulation is found in Table 19-1. The sources of the materials used to prepare the formulation are found in Table 19-2. The components comprising the mini-tablet core are found in Table 19-3. One of skill in the art will appreciate that the specific equipment and sources of materials listed in Tables 19-1 and 19-2 are merely representative of those that may be used by those of ordinary skill in the art to prepare the embodiments of the present invention and are not meant to limit the present invention in any manner.

TABLE 19-1

| Equipment Type | Make/Model |
|---|---|
| High shear granulator | Collette 25 liter |
| Fluid bed dryer | Vector FLM3, 12 liter |
| Mill | Comil |
| Mill | Vector rotary mill |
| V-blender | PK 16 quart |
| Tablet press | Korsch XL100 |
| Coating pan | CompuLab, 15 inch pan |

TABLE 19-2

| Materials | Source |
|---|---|
| Mesalamine | Farchemia |
| Lactose | DMV Fonterra, Pharmatose 200M |
| Hydroxypropylcellulose | Ashland, Klucel EXF |
| Magnesium Stearate | Mallinckrodt |
| Sterile Water | Fisher |
| Ethylcellulose | Ashland, ECN10 |
| Hydroxypropylmethylcellulose | Shin-Etsu, Pharmacoat 603 |
| Triethyl Citrate | Vertellus |
| Ethanol | Spectrum, 190 proof |
| Capsule shells | Capsugel, white 00el |

TABLE 19-3

| Material | % w/w | Weight (g) |
|---|---|---|
| Mesalamine | 80.0 | 4002.6 |
| Pharmatose 200M (lactose) | 17.0 | 849.5 |
| Klucel (dry) (hydroxypropylcellulose) | 2.0 | 100.3 |
| Klucel (binder solution) | 1.0 | about 50 |
| Total | 100.0 | about 5002.4 |
| Water for binder solution | | 769.3 |
| Water for additional granulating | | Up to about 400 |

A hydroxypropyl cellulose solution (Klucel with water) was prepared to an excess of 20% (about 59.9 g Klucel in about 769.3 g water) to allow for adequate pumping of the material into the granulator. Water was added to hydroxypropyl cellulose (Klucel) and mixed until no floating material remained. This took approximately one hour. During this hour, mesalamine, lactose (Pharmatose 200M), and dry hydroxypropyl cellulose (Klucel) were mixed in the granulator for 2 minutes and an initial loss on drying measurement was taken. The granulating solution was then pumped during while running the granulator at impellor a speed of 280 rpm and the chopper at a speed of 1500 rpm. The addition was completed after 2.5 minutes and granulating was continued for one additional minute. The granulation was assessed for cohesiveness and it was determined that more water was needed. Water was added three additional times along with mixing for 1 minute (with the granulation being assessed after each addition). A total of 378 g of additional water was added. The granulation appeared complete as the granulation was cohesive, but still broke apart freely and the agglomerates were small and soft. The granulation was discharged and passed through a mill fitted with a 500Q (square) screen. This screen holes were too large, and did not convey significant milling action. As there were no other screens available near this size and there were no large agglomerates, the process continued into drying.

The drying process was performed in a Vector FLM3. The inlet temperature was set at 60° C. and air flow was set at about 50 cubic feet per minute. The material was dried until the loss on drying (LOD) had each a value of less than 1% (0.57%) which was similar to the starting LOD. This took approximately one half hour. Upon discharge, it was noted that a significant amount of material was adhered to the sides and top of the dryer. This suggests that the airflow could be reduced so that the amount material at the top of the dryer is reduced. Also, a preheating of the dryer may help minimize that material that adheres to the sidewalls.

To help define the milling process and to minimize the creation of fines, milling was performed through series of decreasing screen sizes. The entire batch was initially hand screened through 30-mesh and any oversized material was sent through the mill with a 94R (round) screen. After the mill, the material was hand screened through 30 mesh. Any overs were sent through the mill with a 75R screen. All material was hand screened again. Again, the overs were sent through the mill with a 45R screen. The material was hand screened again and overs sent through the mill with a 24R screen. The material was hand screened one last time and any overs were considered waste. All of the portions were combined and mixed. The resultant material was then blended with about 40.3 g magnesium stearate and considered to be the final blend. Particle size and density testing were performed, see Tables 19-4 and 19-5.

TABLE 19-4

Particle size data for granulation

| Mesh | % Retained |
|---|---|
| 30 | 9.55 |
| 60 | 27.25 |
| 80 | 9.77 |
| 100 | 7.06 |
| 120 | 8.03 |
| 200 | 21.82 |
| Pan | 16.50 |

TABLE 19-5

| Density data for granulation | |
|---|---|
| | Example 19 |
| Bulk Density | 0.540 mg/mL |
| Tapped Density | 0.765 mg/mL |
| Carr's Index* | 29.4 |

*Carr's index = (TD − BD)/TD*100

The data showed that there were many fine materials (200 and pan) in the blend. The impact of the high level of fines could also be seen while visually observing the less than ideal flow of the material in the container. The Carr's index, which gives a general idea about the flowability of the material is significantly higher than 20. Although steps were taken to minimize the creation of a high number of fines during milling, they still were created. The use of a rotary mill may be considered.

EXAMPLE 20

Pharmaceutical Formulation

The pharmaceutical formulation of Example 20 was prepared according to the procedures of Example 19, but with the following changes. Dry mixing took place for 2 minutes at impeller speed of 280 rpm and a chopper speed of 1500 rpm. A total of about 697 g of granulating solution were added while mixing using an impeller speed of 280 rpm and a chopper speed of 1500 rpm for a total of 4 minutes. The chopper speed was then increased to 3000 rpm and mixing was continued for additional 1 minute. The sides and bottom of the granulator were scraped and then about 374 mL of water was added while mixing was continued using an impellor speed of 280 rpm and chopper speed of 1500 rpm for 2 minutes. The increased chopper speed may not be necessary. Also, after the completion of the granulation, it was determined that the material was slightly over-granulated (too cohesive). This result was likely due to either the increased chopper speed or amount of water added, or a combination of both. The material, however, was still considered acceptable and the process continued to the drying step.

The dryer was pre-heated to about 60° C. prior to material being added and the airflow was reduced from about 50 cubic feet per minute to about 35 cubic feet per minute. The drying time required to achieve a loss on drying of less than 1% was consistent was about 30 minutes. The resulting granules were then hand screened through 30 mesh. The overs were sent through a rotary mill with a 30 mesh (585 grams) or 20 mesh (2604 grams) screen. The milled granules were mixed together and then blended with about 47.6 g magnesium stearate. The blend was analyzed for particle size and density.

TABLE 20-1

| Particle size distribution | |
|---|---|
| Mesh | % Retained |
| 30 | 22.41 |
| 60 | 43.26 |
| 80 | 7.67 |
| 100 | 4.28 |
| 120 | 5.08 |
| 200 | 8.67 |
| Pan | 9.06 |

TABLE 20-2

| Density data for granulation | |
|---|---|
| | Example 20 |
| Bulk Density | 0.535 mg/mL |
| Tapped Density | 0.685 mg/mL |
| Carr's Index | 21.9 |

The batch showed good flow during the visual assessment in the container and was used in the tablet compression step. A Korsch XL100 tablet press was tooled with 6 sets of multi-tip punches with 6, 2.25 mm tips each. The target drug load for each mini-tablet core is about 7.8 mg of mesalamine. The press speed was set to 70 rpm and settings were adjusted until the weight and hardness wore within specification. This setup period took a short period of run time, approximately 10 minutes and then usable material was collected. It required about 2 hours to complete the entire 5 kg batch. During the run, no changes were made to the settings and the tablets remained within specifications. The manufacturing process then continued with coating.

The coating solution was prepared to a batch size of 2 kg with a percent solids content of 4.5%. Table 20-3 identifies the components of the coating solution formulation.

TABLE 20-3

| Coating Solution Formulation | | |
|---|---|---|
| Material | % w/w | Weight (g) |
| Ethylcellulose (ECN10) | 2.05 | 40.91 |
| HPMC (603) | 2.05 | 40.92 |
| Triethylcitrate | 0.41 | 8.23 |
| Ethanol | 95.50 | 1910.0 |
| Total | 100.00 | 2000.06 |

Note:
Triethylcitrate is 10% of total polymer content

The coating process used a ¼JAU from Spraying Systems spray gun fitted with a 40100 anti-bearding tip and nozzle. The parameters for the coating process are identified in Table 20-4.

TABLE 20-4

| Coating pan parameters | |
|---|---|
| Parameter | Setpoint |
| Spray rate | About 13.7 to about 14.5 g/min |
| Product temperature | About 25° C. to about 30° C. |
| Air volume | About 147 to about 151 cfm |
| Pan speed | About 10 rpm |
| Atomization air | About 16 to about 17 psi |

The mini-tablet cores were pre-heated in the pan until they were at a temperature of about 25° C. to about 30° C. and the coating solution was sprayed on the mini-tablet cores. There was no tablet sticking, nor was there any bearding present on the spray tip. In order to identify the appropriate weight gain for the desired dissolution profile, tablet samples were taken during the coating process at specified theoretical weight gains. Samples wore taken at about 2.6%, about 2.8%, about 3.0%, and about 3.2% weight gains. The process was considered complete after a weight gain of about 3.4%. At that point, the inlet temperature was increased to 45° C. and the tablets were dried in the pan for about 30 minutes. Table 20-5 lists the theoretical weight gain, followed by a calculated actual weight gain. The overall efficiency of the coating run was calculated to be 77%.

TABLE 20-5

Theoretical and actual coating weight gains

| Theoretical Wt Gain (%) | Actual Wt Gain (%) |
|---|---|
| 2.6 | 1.99 |
| 2.8 | 2.20 |
| 3.0 | 2.43 |
| 3.2 | 2.77 |
| 3.4 | 2.62* |

*This weight is lower than the previous value due to the drying process that this sample underwent. This value was also used to calculate overall efficiency.

Figure 1:
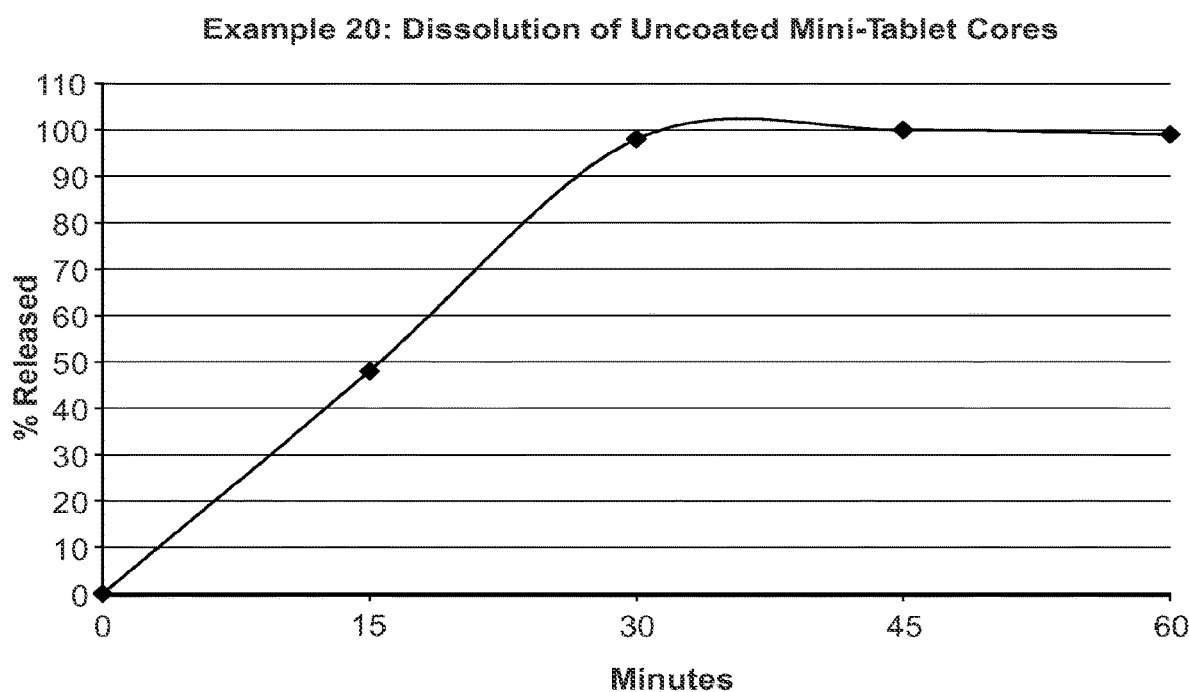
FIG. 1 shows the dissolution profile of uncoated mini-tablet cores according to Example 20.

All of these weight gain samples and the uncoated mini-tablet cores were subjected to a dissolution test. Size 00EL capsule shells were filled with sixty-four tablets for each sample. The capsules with the coated mini-tablets were tested through 8 hours according to the USP monograph for extended release mesalamine capsules (37° C., pH 7.5 phosphate media, paddle apparatus, 100 rpm), whereas the uncoated cores were only tested for one hour using the same methodology. The dissolution profiles generated can be seen FIG. 1. The dissolution data show that the uncoated cores are immediate release in nature.

Figure 2:
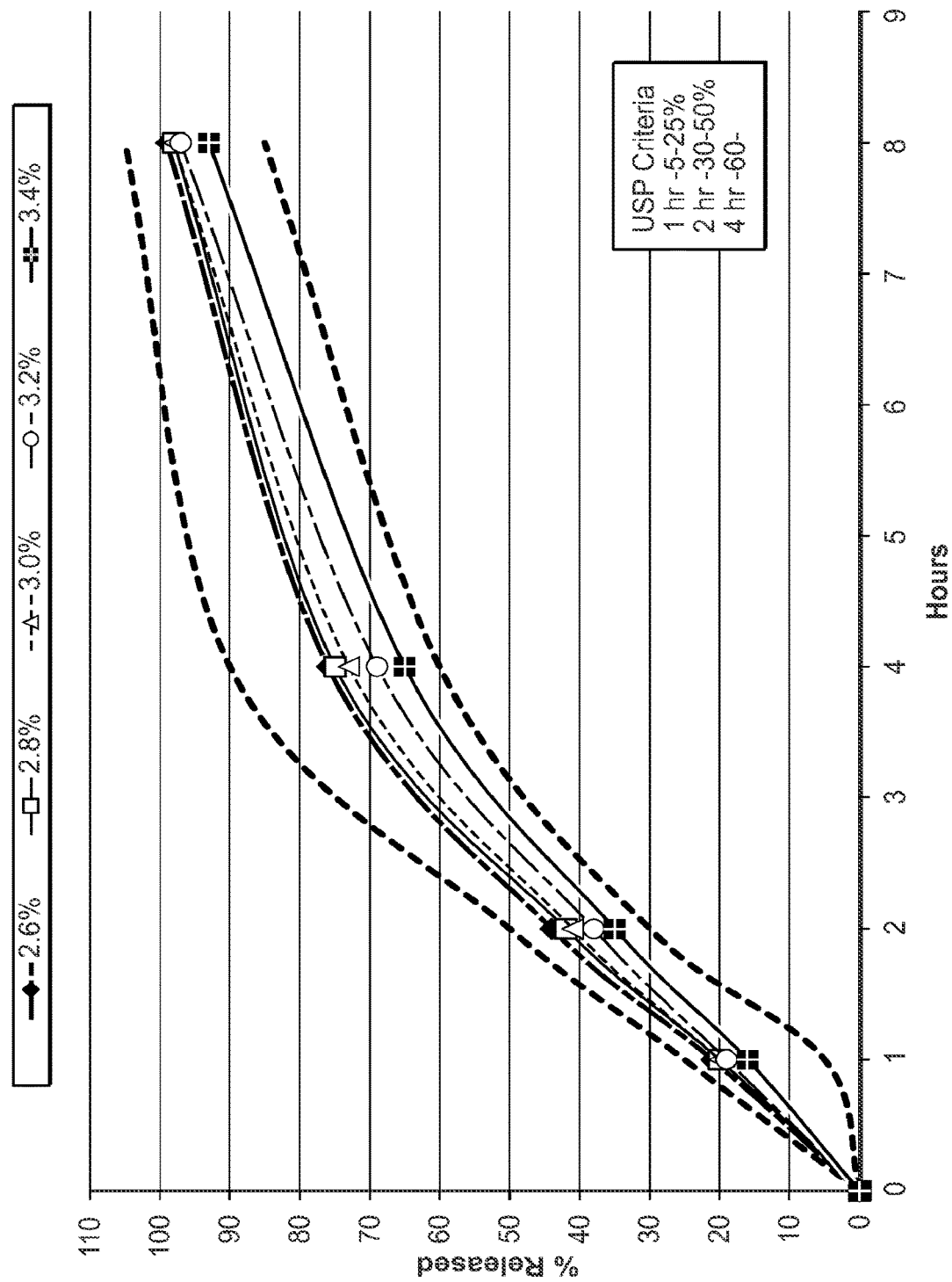
FIG. 2 shows the dissolution profile of capsules comprising coated mini-tablets prepared according to Example 20. The 2.6%, 2.8%, 3.0%, 3.2% and 3.4% coated weight gains shown in FIG. 2 are the theoretical gains for each coated mini-tablet. The actual coating weight gains, according to Example 20, were 1.99%, 2.20%, 2.43%, 2.77% and 2.62%, respectively.

Capsules comprising various coated mini-tablets were prepared according to Example 19 with each capsule comprising 64 mini-tablets (i.e., about 500 mg mesalamine total). These capsules were subjected to a dissolution test in which samples were taken through 8 hours according to the USP monograph for extended release mesalamine capsules (37° C., pH 7.5 phosphate media, paddle apparatus, 100 rpm). The dissolution profiles generated can be seen in FIG. 2. These data demonstrate that all of the weight gain samples taken meet the USP requirements (inside the black dotted lines). The data also show that as additional coating weight was added, the dissolution profile rate decreased, as expected. Based on the results, a target theoretical weight gain of 3.0% was shown to be an advantageous embodiment.

Example 21

Pharmaceutical Formulation

The pharmaceutical formulation of Example 21 was prepared according to the procedures of Example 20, but with the following changes. The granulation step used a chopper speed of 1500 rpm, approximately 350 mL of additional water was added to the granulation mixture, a rotary mill was used for milling of the wet granulation, and the uncoated mini-tablets were coated to a theoretical weight gain of about 3.0%. The components of the granulation are shown in Table 21-1, below.

TABLE 21-1

| Material | % w/w | Weight (g) |
|---|---|---|
| Mesalamine | 80.0 | 4001 |
| Pharmatose 200M (lactose) | 17.0 | 850.9 |
| Klucel (dry) (hydroxypropylcellulose) | 2.0 | 100.3 |
| Klucel (binder solution) | 1.0 | about 50 |
| Total | 100.0 | about 5002.2 |

The granulating procedure for this batch was performed according to the Example 19, with the following changes. The dry mixing step was conducted for about 2 minutes using an impeller speed of 280 rpm and a chopper speed of 1500 rpm, approximately 689 g of granulating solution was added while mixing was performed using an impellor speed of 280 rpm and a chopper speed of 1500 rpm for a total of 5 minutes. The sides of granulator were scraped and then about 350 mL of water were added while mixing was continued at an impellor speed of 280 rpm and chopper speed of 1500 rpm for about 2 minutes. The sides and bottom of the granulator were scraped and the granulation was then mixed for one additional minute. The resulting wet material was passed through a rotary mill affixed with an 8 mesh screen. Any materials that would not pass through the screen were then hand screened through an 8 mesh screen. The drying process was conducted in the same manner as in Example 19. The dryer was pre-heated to about 60° C. and the air volume was about 35 cubic feet per minute. The time required achieve a loss on drying of less than 1% was about 30 minutes. The resulting dried granules were hand screened through 30 mesh. Any overs were sent through a rotary mill affixed with a 20 mesh screen. All of the granules were then combined and blended with about 47.9 g magnesium stearate. The resultant blend was the analyzed for particle size and density, which are shown in Tables 21-2 and 21-3, respectively.

TABLE 21-2

Particle size

| Mesh | % Retained |
|---|---|
| 30 | 15.60 |
| 60 | 37.51 |
| 80 | 9.38 |
| 100 | 7.85 |
| 120 | 4.59 |
| 200 | 14.58 |
| Pan | 10.5 |

TABLE 21-3

Density data

| | Example 21 |
|---|---|
| Bulk Density | 0.561 mg/mL |
| Tapped Density | 0.728 mg/mL |
| Carr's Index | 22.9 |

The particle size profile of Example 21 was in between that of Examples 19 and 20 and demonstrated good flow properties during the visual assessment in the container. The granulation prepared according to this example was compressed into mini-tablets according the same procedures used in Example 20. The target drug load for each mini-tablet core is about 7.8 mg of mesalamine.

Figure 3:
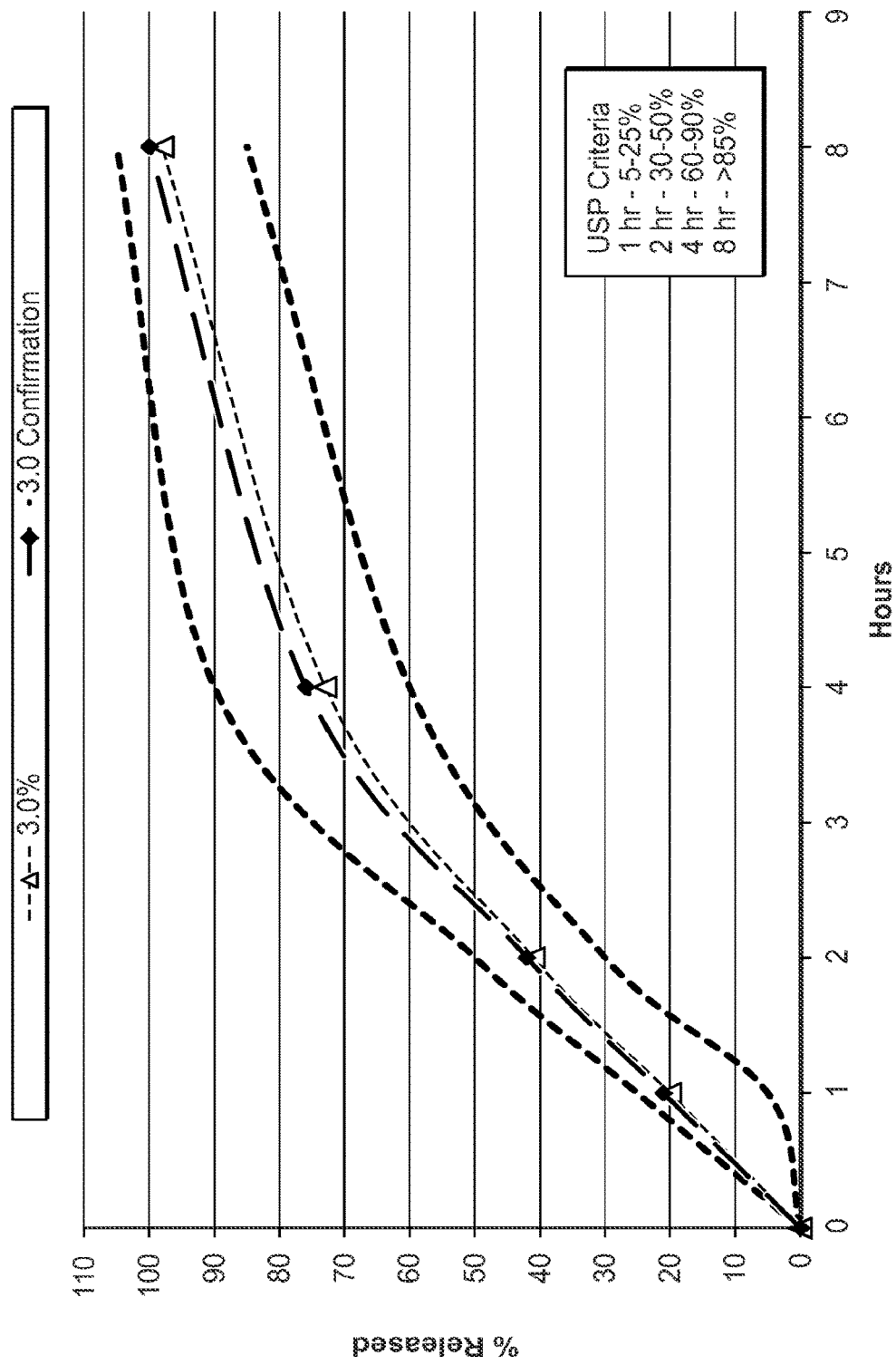
FIG. 3 shows the dissolution profile of capsules comprising coted mini-tablets prepared according to Example 21. The 3% coated weight gains shown in FIG. 3 are theoretical gain for each coated mini-tablet. The actual coating weight gain, according to Example 21, was about 2.6%.

The resulting mini-tablets were coated using the process described in Example 20 to afford coated mini-tablets that demonstrated a weight gain of about 3%. Once the target weight gain of about 3.0% was reached, the inlet temperature was increased to 45° C. and the resulting mini-tablets were dried for about 30 minutes. Once dried, the actual weight gain of the coated mini-tablets was determined to be about 2.6% with a coating efficiency of about 87%. Samples of the mini-tablets were then encapsulated (with each capsule comprising 64 mini-tablets (about 500 mg mesalamine total)) and tested for dissolution according to the methods described in Example 20. The dissolution profiles generated can be seen in FIG. 3.

Example 22

Pharmaceutical Formulation

The pharmaceutical formulation of Example 22 was prepared according to the procedures of Example 20, except with the following changes. The granulation mixture was dry mixed for 2 minutes using an impellor speed of about 290 rpm and a chopper speed of about 1760 rpm, about 690 g of the granulating solution was added to the mixture while mixing continued using an impellor speed of about 280 rpm and a chopper speed of about 1760 rpm for a total of about 5 minutes. The sides and bottom of the granulator were scraped and about 390.7 g of water were added while mixing continued using an impellor speed of about 290 rpm and a chopper speed of about 1760 rpm for about 2 minutes. The resulting wet granulation material was then passed through a rotary mill affixed with an 8 mesh screen. Prior to performing the drying process, the dryer was pre-heated to 60° C., the air flow was set to about 35 cubic feet per minute, and the material was dried to a loss on drying of less than about 1%.

The resulting dried granulation material was hand screened through 30 mesh. Any overs were sent through a rotary mill affixed with a 20 mesh screen and then through a 20 mesh hand screen. Any oversized material from the hand screen was sent back through a mill and the process was repeated until all material passed through the 20 mesh. The resulting granules were combined and blended with magnesium stearate. Particle size and density were analyzed for the resulting mixture and the data is shown in Tables 22-1 and 22-2, respectively.

TABLE 22-1

| Particle size | |
|---|---|
| Mesh | % Retained |
| 30 | About 29 |
| 60 | About 40 |
| 80 | About 8 |
| 100 | About 5 |
| 120 | About 5 |
| 200 | About 10 |
| Pan | About 4 |

TABLE 22-2

| Density data | |
|---|---|
| | Example 22 |
| Bulk Density | 0.543 |
| Tapped Density | 0.692 |
| Carr's Index | 21.5 |

Compression of the granulate into mini-tablets was performed according to the procedures in Example 20. The target drug load for each mini-tablet core is about 7.8 mg of mesalamine.

Figure 4:
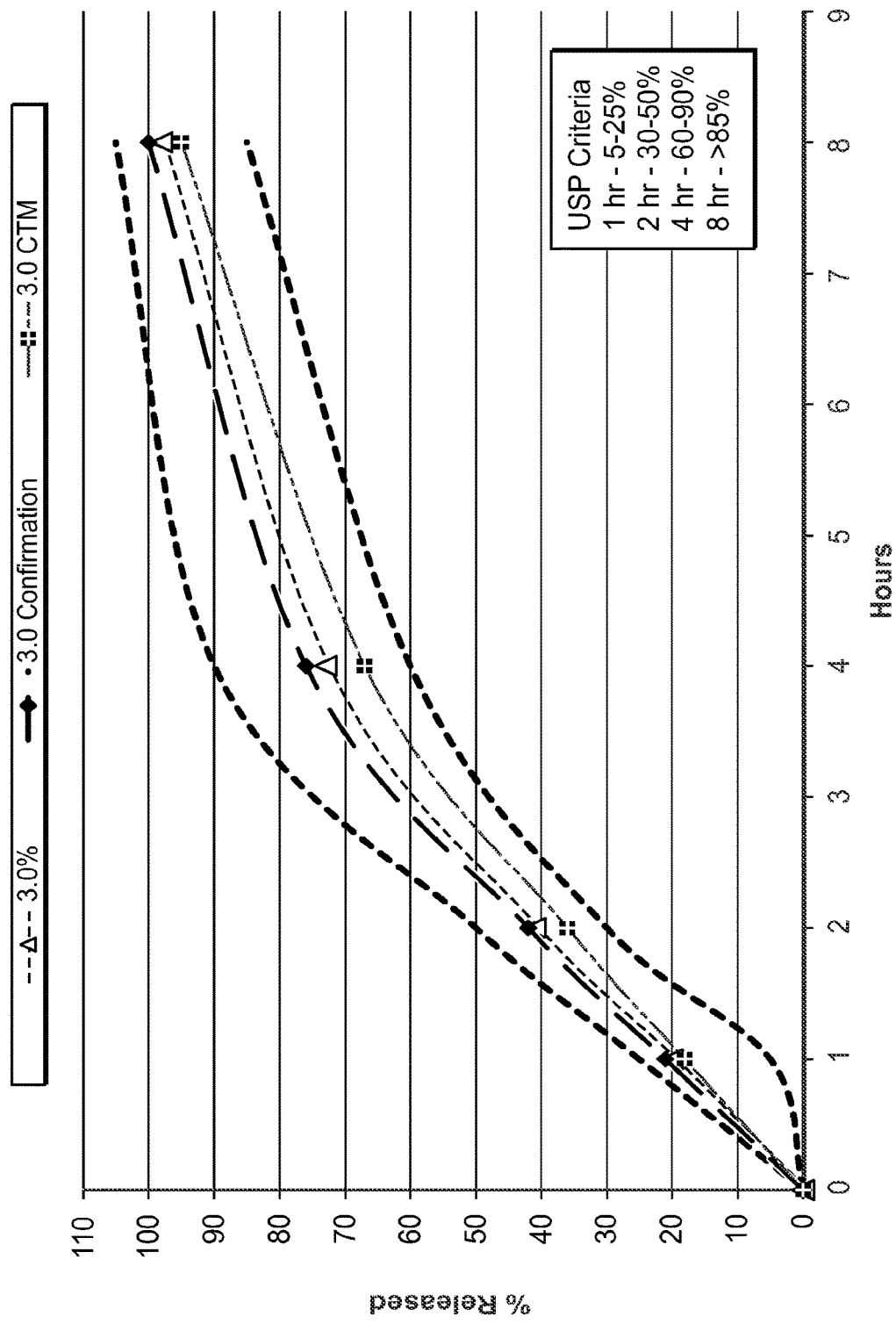
FIG. 4 shows the dissolution profile of capsules comprising coated mini-tablets prepared according to Example 22. The 3% coated weight gains shown in FIG. 4 are theoretical gains for each coated mini-tablet. The actual coating weight gain for the batch labeled "CTM," according to Example 22, was about 2.2%.
Figure 5A:
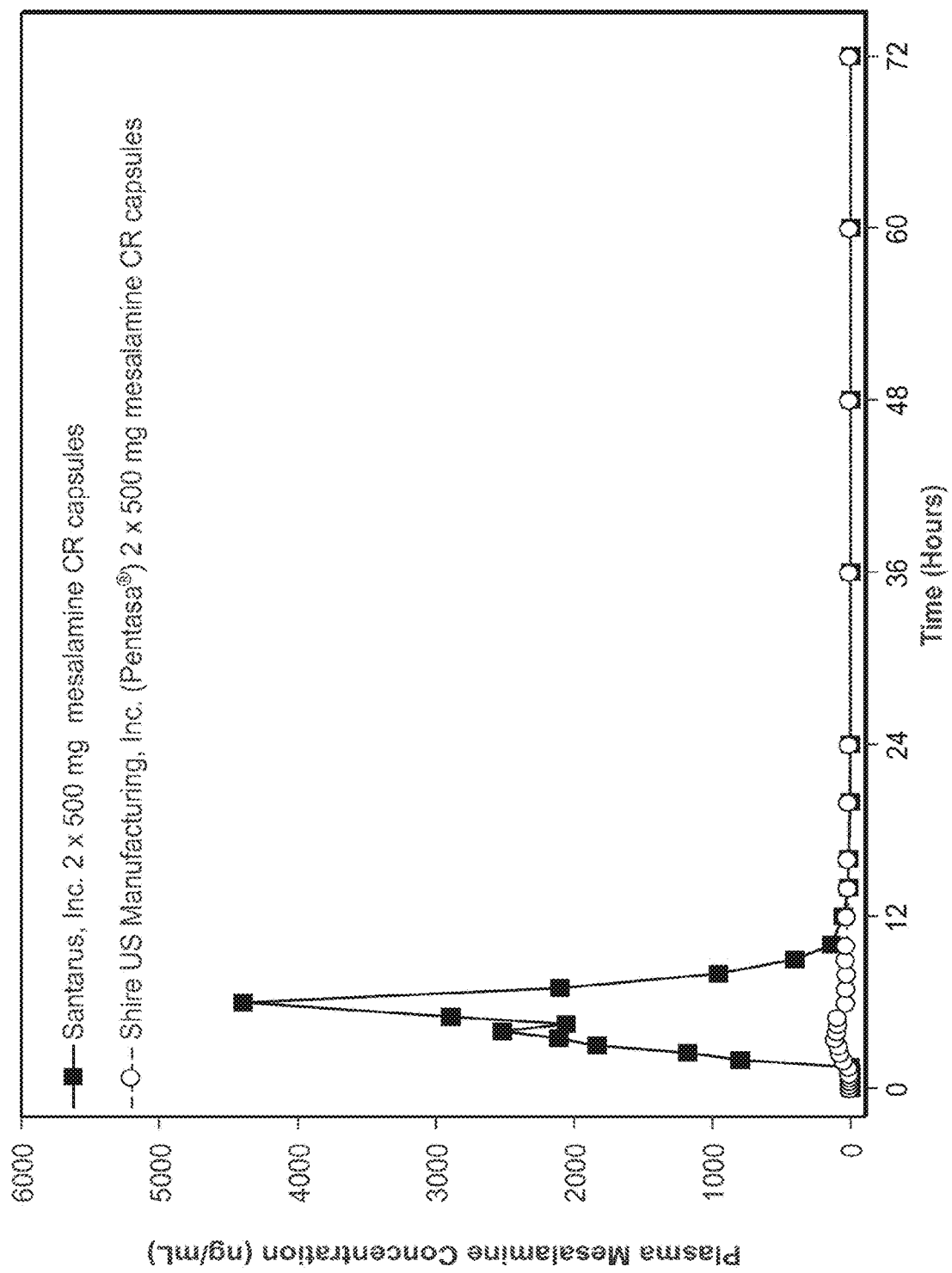
FIGS. 5A-5D depict the mean plasma mesalamine concentrations versus time following administration of treatments A and B.
Figure 5B:
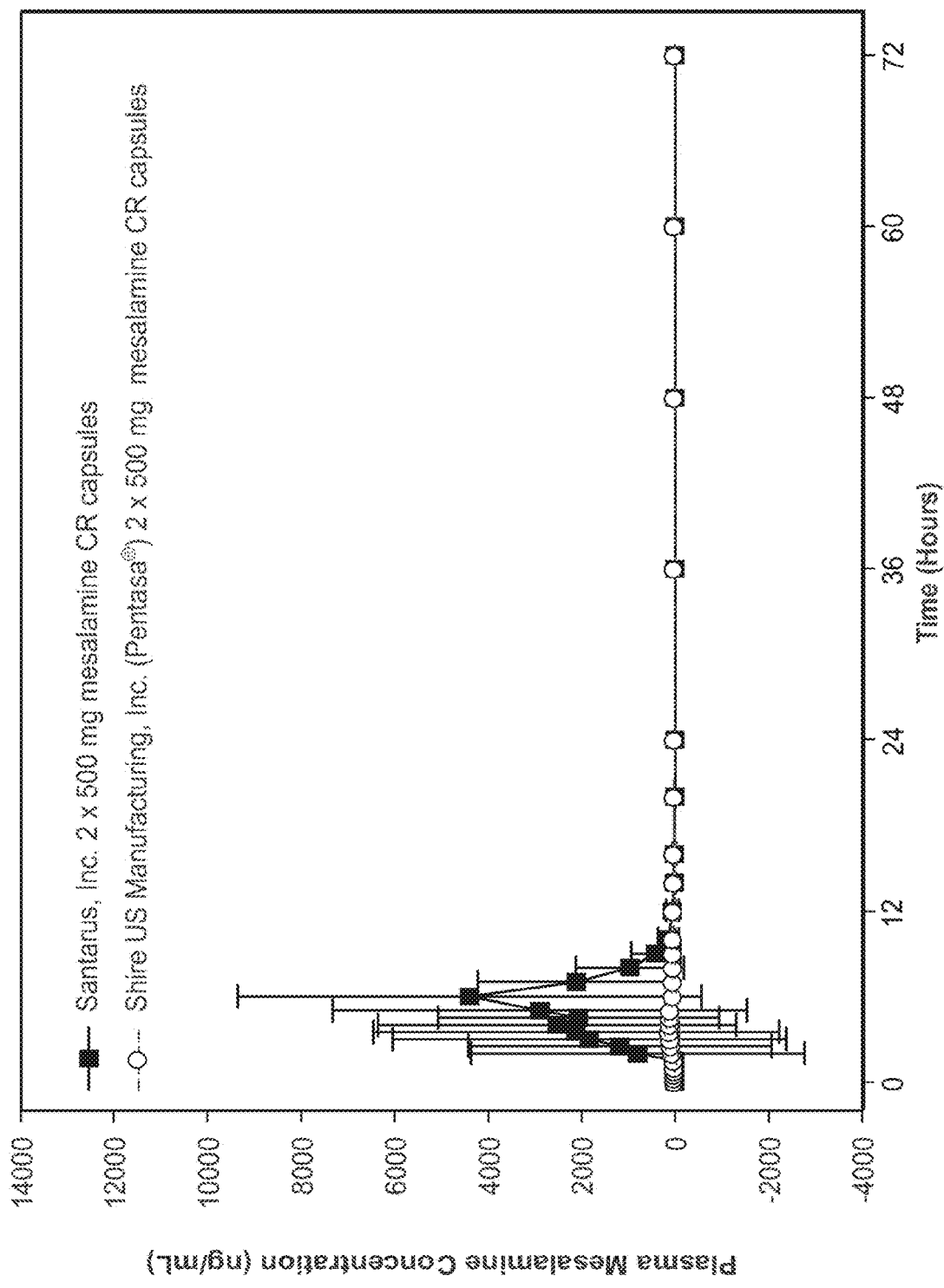
Figure 5C:
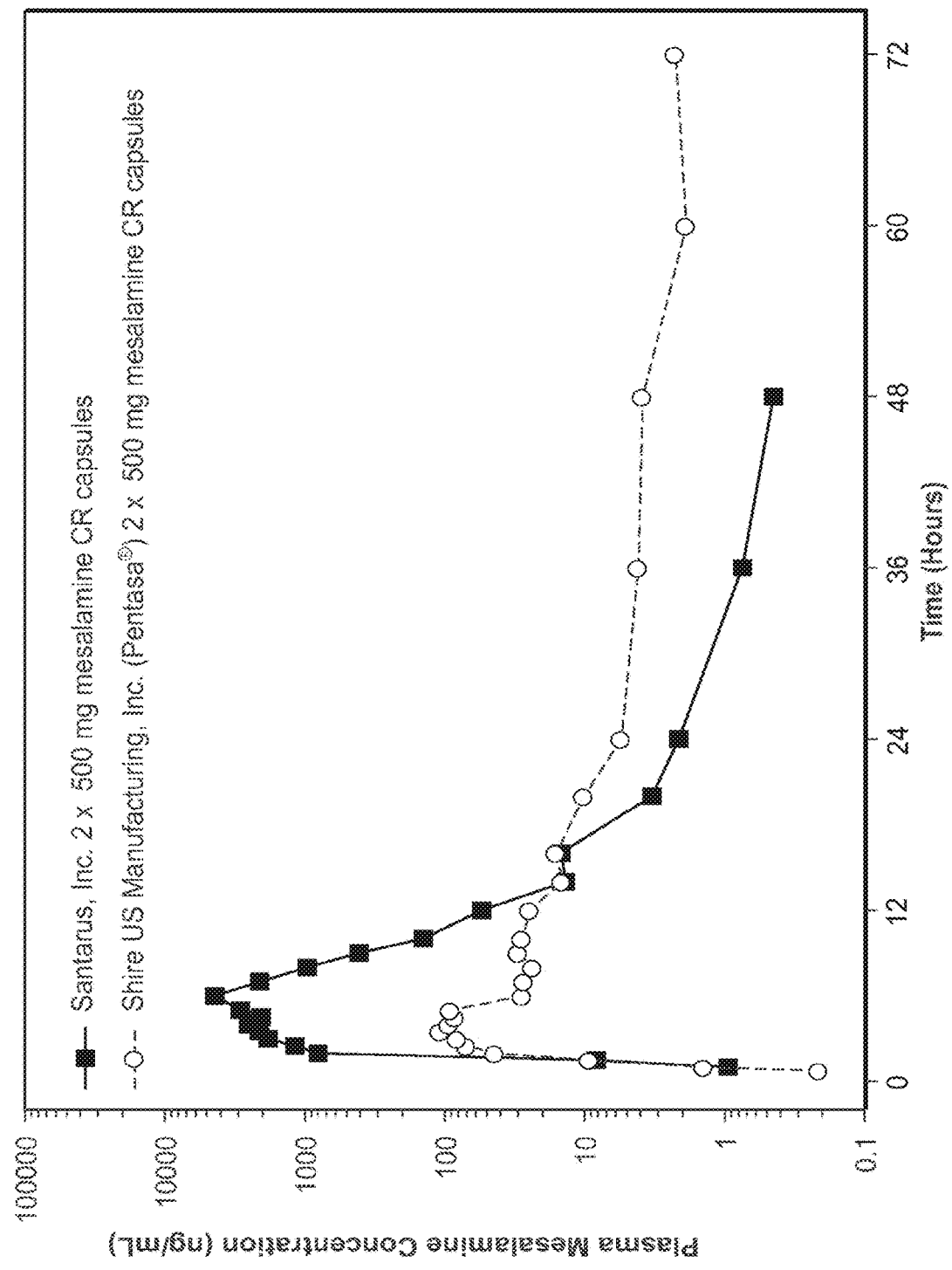
Figure 5D:
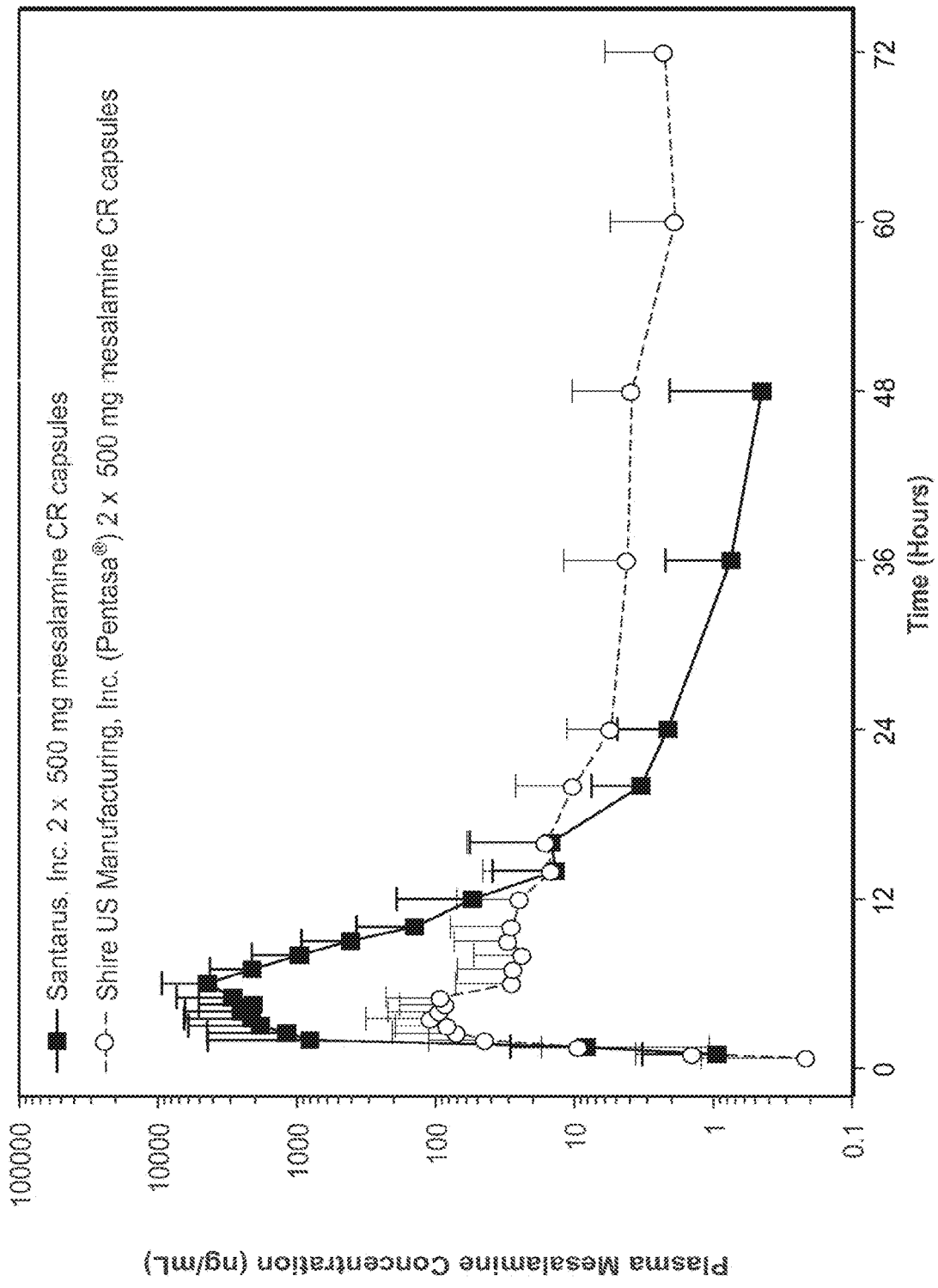

Coating of the mini-tablets was performed according to the procedures in Example 20. The actual weight of the mini-tablets upon being coated was about 2.2%, providing a coating efficiency of about 73%. The coated mini-tablets were encapsulated (with each capsule comprising 64 mini-tablets (about 500 mg mesalamine total)) and tested for dissolution according to the procedures described in Example 20 and the dissolution profiles generated can be seen in FIG. 4.

The remaining coated mini-tablets were encapsulated by placing 64 tablets in white 00EL capsules shells. Fifty filled capsules were then placed into 100 cubic centimeter high-density polyethylene bottles and heat sealed and a total of 61 bottles were packaged.

Example 23

Pharmacokinetic Topline Results

Overview

Comparative, Randomized, Single-Dose, Two-way Crossover Bioavailability Study of Treatment A and Treatment B Following a 1000 mg Dose in Healthy Adult Volunteers Under Fed Conditions Objective The primary objective was to assess the single-dose relative bioavailability of Treatment A and Treatment B following a 1000 mg dose, under fed conditions.

Treatment Descriptions

Test Treatment

Treatment A—500 mg mesalamine controlled-release capsules, having the composition as described in Example 21

Reference Treatment

Treatment B=Shire US Manufacturing, Inc., (Pentasa®) 500 mg mesalamine controlled-release capsules Pentasa® (mesalamine) 500 mg Controlled-Release Capsules Manufactured by Shire US, Inc.

Lot No.: A74595A

Expiration date: 03/2015

Study Design and Methods

This was an open-label, randomized, 2-way crossover, 2-sequence, comparative bioavailability study under fed conditions. There was a 7-day washout period between treatments.

Twenty-four (24) healthy adult non-tobacco-using male and female subjects were enrolled.

Subjects were housed from at least 10 hours before dosing up to the 36-hour blood draw. Subjects were to return for the 48-, 60-, and 72-hour blood draws.

Subjects were dosed with each treatment once according to the randomization schedule. A single oral 1000 mg dose (2×500 mg capsules) was administered with 240 mL of water in the morning at Hour 0, 30 minutes after administration of a standard high-fat breakfast.

TABLE 23-1

| Treatment Sequences | | |
|---|---|---|
| Treatment Sequence | Period 1 | Period 2 |
| 1 (n = 12) | Treatment A | Treatment B |
| 2 (n = 12) | Treatment B | Treatment A |

Serial blood samples (1×3 mL) for assessment of mesalamine plasma concentrations were collected in blood collection tubes containing $K_2EDTA$ before dosing (0 hour) and at the following times post-dose: 0.25, 0.5, 0.75, 1, 1.5, 2, 2.5, 3, 3.5, 4, 4.5, 5, 6, 7, 8, 9, 10, 12, 14, 16, 20, 24, 36, 48, 60, and 72 hours.

Plasma concentrations of mesalamine were determined using a LC/MS/MS method validated with respect to accuracy, precision, linearity, sensitivity, and specificity at Celerion (Lincoln, Nebr.). The analytical ranged used for the analysis of mesalamine was 3.00-1000 ng/mL.

The pharmacokinetic (PK) parameters listed table below were calculated from individual plasma concentration-time data using PhAST® 2.3-001.

Various abbreviations are defined as follows:

| | |
|---|---|
| $AUC_{0-t}$ (ng·h/mL) | The area under the plasma concentration versus time curve, from time 0 to the last measurable concentration ($C_{last}$), as calculated by the linear trapezoidal method. |
| $AUC_{0-inf}$ (ng·h/mL) | The area under the plasma concentration versus time curve from time 0 to infinity. $AUC_{0-inf}$ was calculated as the sum of $AUC_{0-t}$ plus the ratio of the last measurable plasma concentration to the elimination rate constant ($C_{last}/k_{el}$). |
| $AUC_{t1-t2}$ (ng·h/mL) | The area under the plasma concentration versus time curve, from time $t_1$ to $t_2$ hour post-dose, as calculated by the linear trapezoidal method where $t_1$ and $t_2$ are the beginning and end of the interval to be calculated. |
| $AUC_{0-t}/AUC_{0-inf}$ | The ratio of $AUC_{0-t}$ to $AUC_{0-inf}$. |
| $C_{max}$ (ng/mL) | Maximum measured plasma concentration over the time span specified. |
| $t_{max}$ (h) | Time of the maximum measured plasma concentration. If the maximum value occurred at more than one time point, $t_{max}$ was defined as the first time point with this value. |
| $k_{el}$ (h$^{-1}$) | Apparent first-order terminal rate constant calculated from a semi-log plot of the plasma concentration versus time curve. The parameter was calculated by linear least-squares regression analysis using the maximum number of points in the terminal log-linear phase (e.g. three or more non-zero plasma concentrations). |
| $t_{1/2}$ (h) | Apparent first-order terminal half-life calculated as $0.693/k_{el}$. |
| MTT (h) | Mean transit time of a molecule from the time of its entry into the compartment to its time of exit, as calculated $AUMC_{0-inf}/AUC_{0-inf}$. Where $AUMC_{0-inf}$ was the area under the first moment of the concentration-time curve from time 0 extrapolated to infinity. |

Linear regressions for the determination of the $k_{el}$ were performed using at least 3 data points after the $C_{max}$. The $k_{el}$ was not assigned if the terminal elimination phase was not apparent, or if the R$^2$ value was less than 0.8. In cases where the $k_{el}$ interval was not assigned, the values for $AUC_{0-inf}$, $AUC_{0-t}/AUC_{0-inf}$ and $t_{1/2}$ were not calculated.

Statistical Plans

Analysis of Variance

An Analysis of Variance (ANOVA) was performed on the ln-transformed $AUC_{0-t}$, $AUC_{0-inf}$ and $C_{max}$ and partial AUCs. The ANOVA model included sequence, formulation, and period as fixed effects, and subject nested within sequence as a random effect. Sequence was tested using subject nested within sequence as the error term at a 10% level of significance. Each ANOVA included calculation of least-squares means (LSM), the difference between formulation LSM, and the standard error associated with this difference. The above statistical analyses were done using the PROC GLM procedure in SAS® Version 6.12.

Ratios and Confidence Intervals

Ratios of LSM were calculated using the exponentiation of the difference between formulations LSM from the analyses on the ln-transformed $AUC_{0-t}$, $AUC_{0-inf}$ and $C_{max}$ and partial AUCs. These ratios were expressed as a percentage relative to the reference formulation.

Consistent with the two one-sided tests for bioequivalence, 90% confidence intervals (CIs) for the ratios were derived by exponentiation of the CIs obtained for the difference between formulation LSM resulting from the analyses on the in-transformed $AUC_{0-t}$, $AUC_{0-inf}$ and $C_{max}$ and partial AUCs. The CIs were expressed as a percentage relative to the reference formulation.

The primary endpoints were the 90% CIs of the ratios of LSM derived from the analyses on the ln-transformed PK parameters $AUC_{0-t}$, $AUC_{0-inf}$ and $C_{max}$ of the test to reference formulation. Exploratory endpoints were the 90% CI of ratios of LSMs derived from the analyses on the ln-transformed partial AUCs of the test to reference formulation.

Results

Twenty-four (24) healthy adult non-tobacco using subjects were dosed and 23 subjects completed the study and had evaluable mesalamine PK data for each treatment. Subject 20 withdrew from the study between Period 1 and Period 2 due to personal reasons.

The mean plasma mesalamine concentration-time profiles following Treatments A and B are presented in FIG. 5.

Following a single oral 1000 mg dose (2×500 mg capsules), mean peak and extent of exposure for plasma concentrations of mesalamine were not comparable for Treatment A when compared to Treatment B 500 mg mesalamine controlled-release capsules.

After drug administration, mesalamine was rapidly absorbed. The median peak plasma concentrations were reached approximately 6 and 4 hours post-dose for Treatment A and Treatment B, respectively. Mean mesalamine concentrations declined in a multi-exponential manner and remained above the lower limit of quantitation (LLOQ) up to 14 hours post-dose for most subjects.

All of the PK parameters for mesalamine for each treatment are summarized in Table 23-2 and Table 23-3.

TABLE 23-2

Summary of the Pharmacokinetic Parameters of Plasma Mesalamine Following Administration of Treatments A and B

| Pharmacokinetic Parameters | Treatment A (N = 23) | Treatment B (N = 23) |
|---|---|---|
| | Geometric Mean (Geometric CV %) | |
| $AUC_{0-t}$ (ng·h/mL) | 11132 (139) | 578 (118) |
| $AUC_{0-inf}$ (ng·h/mL) | 13741 (118) | 557 (193) |
| | (N = 15) | (N = 8) |
| $C_{max}$ (ng/mL) | 4901 (207) | 155 (130) |
| | Median (Min-Max) | |
| $t_{max}$ (hr) | 6.00 (2.00-9.00) | 4.00 (2.00-20.00) |
| | Arithmetic Mean ± SD | |
| $t_{1/2}$ (hr) | 3.60 ± 3.44 | 8.61 ± 8.53 |
| | (N = 15) | (N = 8) |
| $AUC_{0-t}/AUC_{0-inf}$ (%) | 99.7 ± 0.647 | 93.2 ± 3.49 |
| | (N = 15) | (N = 8) |

TABLE 23-3

Summary of the Pharmacokinetic Parameters of Plasma Mesalamine Following Administration of Treatments A and B

| Pharmacokinetic Parameters | Treatment A (N = 23) | Treatment B (N = 23) |
|---|---|---|
| | Geometric Mean (Geometric CV %) | |
| $AUC_{0-1}$ (ng·h/mL) | 0.118 (243)* | 0.228 (199)* |
| $AUC_{0-2}$ (ng·h/mL) | 9.34 (904) | 10.2 (169) |
| | (N = 17) | (N = 21) |
| $AUC_{0-4}$ (ng·h/mL) | 411 (2916) | 94.0 (153) |
| | (N = 22) | |
| $AUC_{0-6}$ (ng·h/mL) | 4321 (400) | 197 (140) |
| $AUC_{0-7}$ (ng·h/mL) | 7081 (272) | 221 (133) |

TABLE 23-3-continued

Summary of the Pharmacokinetic Parameters of Plasma Mesalamine Following Administration of Treatments A and B

| Pharmacokinetic Parameters | Treatment A (N = 23) | Treatment B (N = 23) |
| --- | --- | --- |
| $AUC_{0-24}$ (ng · h/mL) | 11089 (140) | 487 (107) |
| $AUC_{1-6}$ (ng · h/mL) | 4321 (400) | 197 (141) |
| $AUC_{2-4}$ (ng · h/mL) | 390 (3058) | 81.4 (164) |
|  | | (N = 22) |
| $AUC_{4-t}$ (ng · h/mL) | 8550 (131) | 346 (222) |
| $AUC_{6-7}$ (ng · h/mL) | 1632 (275) | 16.6 (127) |
|  |  | (N = 22) |
| $AUC_{6-12}$ (ng · h/mL) | 3635 (176) | 84.1 (234) |
|  |  | (N = 22) |
| $AUC_{6-24}$ (ng · h/mL) | 3957 (147) | 151 (310) |
|  |  | (N = 22) |
| $AUC_{12-24}$ (ng · h/mL) | 68.4 (145) | 74.8 (325) |
|  |  | (N = 19) |
| Arithmetic Mean ± SD | | |
| MTT | 6.28 ± 2.31 (N = 15) | 11.6 ± 7.18 (N = 8) |

*Arithmetic mean and CV

Overall, the LLOQ of the assay (3.00 ng/mL) represented less than 2% of mesalamine mean $C_{max}$. In general, the sampling schedule used to characterize mesalamine in plasma appeared to be robust since the mean ratio of $AUC_{0-t}$ to $AUC_{0-inf}$ across both formulations was greater than 93%. Based on visual inspection of the mesalamine concentration-time profiles, 8 subjects administered Treatment A and 15 subjects administered Treatment B did not appear to be in the elimination phase at the end of their profiles. Therefore, the PK parameters $AUC_{0-t}$, $AUC_{0-t}/AUC_{0-inf}$, $t_{1/2}$ and kel could not be estimated and set to missing for these subjects. Hence, these results should be interpreted with caution considering a large number of subjects' elimination profiles could not be well characterized.

Following a single administration of 1000 mg mesalamine (2×500 mg) controlled-release capsule, geometric mean peak exposure to mesalamine was considerably higher for Treatment A relative to Treatment B with $C_{max}$ values of 4901 and 155 ng/mL, respectively, and was reached by 6 and 4 hours after dosing, respectively. The geometric mean extent of exposure to mesalamine showed a similar trend as that seen with the peak exposure, with observed values of 11132 and 578 (ng)(h)/mL ($AUC_{0-t}$) and 13741 and 557 (ng)(h)/mL ($AUC_{0-inf}$). The intersubject variability was very high and ranged between 118 to 207%.

The mean apparent elimination half-life ($t_{1/2}$) of mesalamine does not appear to be comparable following dosing for both formulations and ranged between 3.60 and 8.61 hours in healthy subjects. The half-life for Treatment B, in general, appeared to be longer than that of Treatment A. It should be noted that the elimination half-life could not be estimated for a large number of subjects; hence the results should be interpreted with caution. The observed $t_{1/2}$ in this study most likely does not represent the true elimination $t_{1/2}$. The true elimination $t_{1/2}$ of mesalamine following oral administration of Treatment B cannot be determined because of the continuous release and absorption of mesalamine throughout the GI tract.

The results of the statistical comparisons of the AUC0-t, $AUC_{0-inf}$, $C_{max}$, and partial AUCs of mesalamine are presented in Table 23-4 and Table 23-5.

TABLE 23-4

A summary of statistical comparisons of plasma mesalamine pharmacokinetic parameters $AUC_{0-t}$, $AUC_{0-inf}$, and $C_{max}$: Treatment A versus Treatment B (primary analysis). Mesalamine in Plasma (N = 23)

| PK Parameter | LSM (A) | LSM (B) | Ratio of LSM | 90% CI | Intrasubject CV (%) |
| --- | --- | --- | --- | --- | --- |
| $AUC_{0-t}$* | 11014.369 | 577.075 | 1908.7 | 1144.1-3184.2 | 132.7 |
| $AUC_{0-inf}$* | 14127.747 (N = 15) | 315.238 (N = 8) | 4481.6 | 1851.0-10850.9 | 76.3 |
| $C_{max}$ | 4836.6456 | 154.4538 | 3131.5 | 1615.3-6070.6 | 211.3 |

*The terminal elimination could not be estimated for a many subjects ($AUC_{0-inf}$ could not be calculated) hence the large difference in AUC results.

TABLE 23-5

A summary of statistical comparisons of plasma mesalamine pharmacokinetic parameters -- partial AUCs: Treatment A versus Treatment B (exploratory analysis). Mesalamine in Plasma (N = 23)

| PK Parameter | LSM (A) | LSM (B) | Ratio of LSM | 90% CI | Intrasubject CV (%) |
| --- | --- | --- | --- | --- | --- |
| $AUC_{0-2}$ | 8.34193 (N = 17) | 10.30732 (N = 21) | 80.9 | 24.2-270.8 | 740.2 |
| $AUC_{0-4}$ | 375.6703 (N = 22) | 94.3423 | 398.2 | 123.3-1285.5 | 1263.6 |
| $AUC_{0-6}$ | 4244.513 | 198.608 | 2137.1 | 914.2-4996.1 | 392.0 |
| $AUC_{0-7}$ | 6954.390 | 222.327 | 3128.0 | 1467.2-6669.0 | 286.8 |
| $AUC_{0-24}$ | 10972.770 | 486.738 | 2254.3 | 1368.7-3713.0 | 127.5 |
| $AUC_{1-6}$ | 4244.461 | 198.315 | 2140.3 | 915.3-5004.4 | 392.3 |
| $AUC_{2-4}$ | 358.7940 (N = 22) | 81.8174 | 438.5 | 133.6-1439.1 | 1357.8 |
| $AUC_{4-t}$ | 8415.6907 | 346.8177 | 2426.5 | 1367.2-4306.5 | 160.7 |
| $AUC_{6-7}$ | 1585.4435 | 17.4055 (N = 22) | 9108.9 | 4544.2-18258.9 | 223.1 |
| $AUC_{6-12}$ | 3560.1871 | 86.4223 (N = 22) | 4119.5 | 2121.5-7999.3 | 202.4 |
| $AUC_{6-24}$ | 3888.5610 | 155.0560 (N = 22) | 2507.8 | 1261.4-4985.9 | 217.6 |
| $AUC_{12-24}$ | 68.7374 | 68.7947 (N = 19) | 99.9 | 39.7-251.4 | 365.7 |

The 90% CI of the ratios of LSM derived from the analyses of the ln-transformed PK parameters $AUC_{0-t}$, $AUC_{0-inf}$, $C_{max}$, and partial AUCs of the test to reference formulation for mesalamine in plasma were not within 80-125%.

Based on these results, Treatment A and Treatment B are not bioequivalent under fed conditions.

Safety

Adverse Events

Adverse events (AEs) were monitored throughout the study, until resolution. Adverse events were described in terms of severity, seriousness, outcome, action, frequency and relationship to treatments.

Overall, a total of 18 AEs were experienced by 6 subjects (25% of the study population). Four (4) AEs were considered to be possibly related to Treatment A (Subjects 2 and 23, in Period 1, and Subject 8, in Period 2) and 4 AEs were considered to be possibly related to Treatment B (Subjects 6 and 23 in Period 2 and Subject 8 in Period 1) as judged by the PI. All AEs considered to be possibly related to the study treatments were mild in severity.

Discussion and Conclusions

The peak and overall extent of exposure for Treatment A was significantly higher than that observed for Treatment B.

The peak and overall extent of exposure of both mesalamine formulations were not comparable to each other, with the 90% CIs for the LSMs for $C_{max}$, $AUC_{0-t}$, $AUC_{0-inf}$ and partial AUCs not contained within the 80-125% range.

Peak mesalamine concentrations were reached by 6 and 4 hours following drug administration of Treatment A and Treatment B with a half-life of 3.60 and 8.61 hours, respectively.

Based on visual inspection of the mesalamine concentration-time profiles, 8 subjects administered Treatment A and 15 subjects administered Treatment B did not appear to be in the elimination phase at the end of their profiles. Therefore, the PK parameters $AUC_{0-inf}$, $AUC_{0-t}/AUC_{0-inf}$, $t_{1/2}$ and kel could not be estimated and set to missing for these subjects. Hence, these results should be interpreted with caution considering a large number of subjects' elimination profiles could not be well characterized.

EXAMPLE 24

Combination Treatment

Overview and Protocol

To establish the incremental benefit of budesonide MMX when added to current oral mesalamine therapy, a randomized, double blind, placebo-controlled Phase 3b clinical study of budesonide MMX 9 mg tablets ("budesonide extended release tablets (9 mg)," also known as Uceris™) is conducted in patients with mild or moderate active ulcerative colitis (UC) who are not adequately controlled on background oral mesalamine (5-ASA) therapy, such as the solid dosage forms described herein (e.g., Treatment B).

This Phase 3b study evaluates patients with mild to moderate active ulcerative colitis who continue using their current 5-ASA treatment regimen, such as those described herein (e.g., Treatment B), and, for an 8-week period, add budesonide MMX 9 mg or placebo administered once daily. Approximately 500 patients are enrolled, with 250 in each treatment arm. The patients have been on a therapeutic dose of their oral 5-ASA (defined in this study as mesalamine ≥2.4 g/day, or equivalent dose of another approved 5-ASA) ("background therapy") for a minimum of 6 weeks prior to randomization, and present with signs and symptoms of active, mild to moderate UC (UCDAI score ≥4 and ≤10 with a mucosal appearance score ≥1) in spite of their background therapy. The study compares the two treatment groups over 56 days (8 weeks). Patients remain on the same preparation and dosage strength of their oral 5-ASA for the duration of the study. Eligible patients are randomized to one of the following two treatment arms: 1. Budesonide MMX 9 mg (one tablet); 2. Placebo (tablet indistinguishable from budesonide MMX 9 mg tablet). The assigned study drugs are taken each morning after breakfast. Six visits to the clinical center are scheduled: one at Screening, four during the double-blind treatment period (Day 1, Day 14, Day 28, and Day 56), and one Safety Follow-up Visit 28 days (4 weeks) after the Day 56 visit. At Screening and Visit 5 (Day 56), patients are required to undergo a flexible sigmoidoscopy (or colonoscopy, if clinically indicated) with one photograph and three mucosal biopsies taken from the most severely affected region(s) of the colon visualized during the endoscopy procedure. Patients who are withdrawn early from the study before Day 56 are required to visit the study center as soon as possible so that the final assessments can be conducted.

The primary endpoint of the study is remission at week 8, defined as an Ulcerative Colitis Disease Activity Index (UCDAI) score of less than or equal to 1, with a zero score for rectal bleeding, stool frequency and mucosal appearance.

Patients receiving a combination of 9 mg budesonide MMX and a solid dosage form comprising mesalamine, such as those described herein (e.g., Treatment B), will experience a higher rate of remission of UC than patients receiving placebo.

Tablets comprising 9 mg of budesonide and having the following composition were prepared. Each tablet weighs about 330 mg and can be prepared using the procedures described in United States Patent Application Publication No. 2012-0021052 A1, which is hereby incorporated by reference in its entirety.

| Component | mg/tablet |
| --- | --- |
| Tablet | |
| Budesonide | 9.0 |
| Stearic Acid (lipophilic matrix forming materials) | 10.0 |
| Lecithin (amphiphilic matrix forming material) | 10.0 |
| Microcrystalline cellulose | 156.0 |
| Hydroxypropylcellulose | 60.0 |
| Lactose monohydrate | 50.0 |
| Silica, colloidal hydrated | 2.0 |
| Magnesium stearate | 3.0 |
| Coating materials | |
| Eudragit L100 (methacrylic copolymer, Type A) | 8.0 |
| Eudragit S100 (methacrylic copolymer, Type B) | 8.0 |
| Talc | 7.9 |
| Titanium dioxide | 4.5 |
| Triethylcitrate | 1.6 |
| Alcohol | q.s. |

Coated tablets individually weighing about 330 mg were obtained.

Composition of Budesonide Extended Release Tablets (6 Mg)

Tablets comprising 6 mg of budesonide and having the following composition were prepared having an individual weight of about 330 mg.

| Component | mg/tablet |
| --- | --- |
| Tablet | |
| Budesonide | 6.0 |
| Stearic Acid (lipophilic matrix forming materials) | 10.0 |
| Lecithin (amphiphilic matrix forming material) | 10.0 |
| Microcrystalline cellulose | 156.0 |
| Hydroxypropylcellulose | 60.0 |
| Lactose monohydrate | 53.0 |
| Silicon dioxide | 2.0 |
| Magnesium stearate | 3.0 |
| Coating materials | |
| Eudragit L100 (acrylic and methacrylic copolymer) | 8.0 |
| Eudragit S100 (acrylic and methacrylic copolymer) | 8.0 |
| Talc | 7.9 |
| Titanium dioxide | 4.5 |
| Triethylcitrate | 1.6 |
| Alcohol | q.s. |

Those of ordinary skill in the art will recognize, or be able to ascertain using no more than routine experimentation, many equivalents to the specific embodiments of the invention described herein.

We claim:

1. A controlled-release solid dosage form, comprising a plurality of mini-tablets, wherein each mini-tablet comprises:
   (a) a core, comprising mesalamine; and
   (b) a coating, comprising low-viscosity ethyl cellulose; and a pore-forming agent selected from the group consisting of hydroxypropyl cellulose and hydroxypropyl methylcellulose; wherein the coating surrounds the core.

2. The solid dosage form of claim 1, wherein the core further comprises a diluent.

3. The solid dosage form of claim 1, wherein the core further comprises a binder.

4. The solid dosage form of claim 1, wherein the core further comprises a lubricant.

5. The solid dosage form of claim 1, wherein the coating further comprises a plasticizer.

6. The solid dosage form of claim 1, wherein the number of mini-tablets is about 30 to about 100.

7. The solid dosage form of claim 1, wherein the diameter of the mini-tablets is about 1 mm to about 5 mm.

8. The solid dosage form of claim 1, wherein the viscosity of the low-viscosity ethyl cellulose is less than about 15 cP.

9. The solid dosage form of claim 1, wherein the ratio in the coating of the low-viscosity ethyl cellulose to the pore-forming agent is about 7:3 to about 4:6.

10. The solid dosage form of claim 1, wherein the viscosity of the hydroxypropyl cellulose or hydroxypropyl methylcellulose is about 3 cP to about 15 cP.

11. The solid dosage form of claim 1, wherein the weight percentage of the mesalamine is about 75% to about 85% based on the weight of the core.

12. The solid dosage form of claim 1, wherein the weight percentage of the mesalamine is about 40% to about 90% by weight of the mini-tablet.

13. The solid dosage form of claim 1, wherein the solid dosage form is a capsule; and the capsule comprises the plurality of mini-tablets.

14. The solid dosage form of claim 1, wherein the amount of mesalamine is about 200 mg to about 1,000 mg.

15. The solid dosage form of claim 1, comprising
   (a) a core, comprising mesalamine in about 80% by weight of the core; lactose in about 16% by weight of the core; hydroxypropyl cellulose in about 3% by weight of the core; and a lubricant in about 1% by weight of the core; and
   (b) a coating, comprising low-viscosity ethyl cellulose; a pore-forming agent; and triethyl citrate;
   wherein the coating surrounds the core; and the coating comprises from about 1% to about 6% by weight of the mini-tablet.

16. The solid dosage form of claim 1, wherein the solid dosage form comprises about 500 mg of mesalamine; and oral administration of two of the solid dosage forms to a healthy adult human results in a $C_{max}$ of from about 300 ng/mL to about 7500 ng/mL.

17. The solid dosage form of claim 1, wherein the solid dosage form comprises about 500 mg of mesalamine; and oral administration of two of the solid dosage forms to a healthy adult human results in a $T_{max}$ of from about 5 hours to about 8 hours.

18. The solid dosage form of claim 1, wherein each mini-tablet further comprises an enteric coating.

19. A method of treating, inducing remission of, or maintaining remission of inflammatory bowel disease, comprising the step of orally administering to a mammal in need thereof a therapeutically effective amount of a solid dosage form of claim 1.

20. The method of claim 19, wherein the inflammatory bowel disease is ulcerative colitis or Crohn's disease.

* * * * *